United States Patent
Quave et al.

(10) Patent No.: US 10,195,241 B2
(45) Date of Patent: Feb. 5, 2019

(54) **BOTANICAL EXTRACTS AND COMPOUNDS FROM *CASTANEA* PLANTS AND METHODS OF USE**

(71) Applicants: Emory University, Atlanta, GA (US); University of Iowa Research Foundation, Iowa City, IA (US)

(72) Inventors: Cassandra L. Quave, Decatur, GA (US); James Lyles, Decatur, GA (US); Alexander R. Horswill, Iowa City, IA (US)

(73) Assignees: Emory University, Atlanta, GA (US); University of Iowa Research Foundation, Iowa City, IA (US)

( * ) Notice: Subject to any disclaimer, the term of this patent is extended or adjusted under 35 U.S.C. 154(b) by 15 days.

(21) Appl. No.: 15/192,514

(22) Filed: Jun. 24, 2016

(65) Prior Publication Data
US 2016/0375074 A1    Dec. 29, 2016

Related U.S. Application Data

(60) Provisional application No. 62/185,146, filed on Jun. 26, 2015.

(51) Int. Cl.

| | | |
|---|---|---|
| *A61K 36/00* | (2006.01) | |
| *A61K 36/49* | (2006.01) | |
| *A61K 45/06* | (2006.01) | |
| *A61K 9/00* | (2006.01) | |
| *A61K 8/97* | (2017.01) | |
| *A61Q 19/10* | (2006.01) | |
| *A61L 15/44* | (2006.01) | |
| *A61L 15/58* | (2006.01) | |
| *A61L 15/40* | (2006.01) | |
| *C11D 3/382* | (2006.01) | |
| *C11D 3/20* | (2006.01) | |
| *A61L 15/46* | (2006.01) | |
| *C11D 3/48* | (2006.01) | |

(52) U.S. Cl.
CPC ............... *A61K 36/49* (2013.01); *A61K 8/97* (2013.01); *A61K 9/0036* (2013.01); *A61K 45/06* (2013.01); *A61L 15/40* (2013.01); *A61L 15/44* (2013.01); *A61L 15/46* (2013.01); *A61L 15/58* (2013.01); *A61Q 19/10* (2013.01); *C11D 3/2075* (2013.01); *C11D 3/382* (2013.01); *C11D 3/48* (2013.01); *A61K 2236/15* (2013.01); *A61K 2236/17* (2013.01); *A61K 2236/39* (2013.01); *A61K 2236/55* (2013.01); *A61L 2300/404* (2013.01); *A61L 2300/406* (2013.01)

(58) Field of Classification Search
CPC .................................................... A61K 36/00
See application file for complete search history.

(56) References Cited

U.S. PATENT DOCUMENTS

| | | | |
|---|---|---|---|
| 8,067,044 B2 | 11/2011 | Henry | |
| 2007/0237847 A1* | 10/2007 | Henry | ................ A61K 8/97 424/769 |
| 2012/0034289 A1 | 2/2012 | Maria | |
| 2013/0137647 A1 | 5/2013 | Graziani | |

OTHER PUBLICATIONS

Almeida et al. In vivo Skin Irritation Potential of a *Castanea sativa* (Chestnut) Leaf Extract, a Putative Natural Antioxidant for Topical Application, Basic & Clinical Pharmacology & Toxicology, 2008, 103, 461-467.
Almeida et al. Protective effect of *C. sativa* leaf extract against UV mediated-DNA damage in a human keratinocyte cell line, Journal of Photochemistry and Photobiology B: Biology 144 (2015) 28-34.
Basile et al. Antibacterial and allelopathic activity of extract from *Castanea* sativa leaves, Fitoterapia, 71, 2000, S110-S116.
Boucher et al. Epidemiology of Methicillin-Resistant *Staphylococcus aureus*, Clinical Infectious Diseases, 2008, 46: S344-9.
Braga et al. Castanea sativa by-products: a review on added value and sustainable application, Natural Product Research, 2015, 29,1: 1-18.
Garo et al., Asiatic Acid and Corosolic Acid Enhance the Susceptibility of Pseudomonas aeruginosa Biofilms to Tobramycin, Antimicrobial Agents and Chemotherapy, 2007, vol. 51, No. 5, pp. 1813-1817.
Pieroni et al. Ethnopharmacognostic survey on the natural ingredients used in folk cosmetics, cosmeceuticals and remedies for healing skin diseases in the inland Marches, Central-Eastern Italy, Journal of Ethnopharmacology 91 (2004) 331-344.
Quave et al. Quorum Sensing Inhibitors for *Staphylococcus aureus* from Italian Medicinal Plants, Planta Med. 2011, 77(2): 188-195.
Quave et al. Flipping the switch:tools for detecting small molecule inhibitors of s aphylococcal virulence, Front Microbial. 2014, 5,706, 1-10.
Quave et al. *Castanea sativa* (European Chestnut) Leaf Extracts Rich in Ursene and Oleanene Derivatives Block *Staphylococcus aureus* Virulence and Pathogenesis without Detectable Resistance, 2015, PLoS ONE 10(8): e0136486.
Rangasamy et al. Two anti-staphylococcal triterpenoid acids isolated from *Psiloxylon mauritianum* (Bouton ex Hook.f.) Baillon, an endemic traditional medicinal plant of Mauritius, South African Journal of Botany 93 (2014) 198-203.
Wong et al. Chemical constituents and antibacterial activity of *Melastoma malabathricum* L., Nat Prod Res. 2012;26 (7):609-18.

* cited by examiner

*Primary Examiner* — Qiuwen Mi
(74) *Attorney, Agent, or Firm* — Emory Patent Group

(57) ABSTRACT

This disclosure relates to extracts from chestnut plants and compositions comprising compounds contained therein. In certain embodiments, the extracts are derived from the leaves of a *Castanea* plant. In certain embodiments, the disclosure relates to methods of treating or preventing bacterial infections, acne, and other related uses.

3 Claims, 16 Drawing Sheets

BOTANICAL EXTRACTS AND COMPOUNDS FROM *CASTANEA* PLANTS AND METHODS OF USE

CROSS REFERENCE TO RELATED APPLICATIONS

This application claims the benefit of priority to U.S. Provisional Application No. 62/185,146 filed Jun. 26, 2015, hereby incorporated by reference in its entirety for all purposes.

STATEMENT REGARDING FEDERALLY FUNDED RESEARCH

This invention was made with government support under R01AT007052 awarded by NIH (NCCIH). The government has certain rights in the invention.

BACKGROUND

Since the widespread introduction of antibiotics in the 1940s, the same storyline has repeated itself over and over again: new antibiotic is introduced and then resistant variants emerge and quickly spread, effectively limiting the utility and lifespan of the drug. From an evolutionary biology perspective, this is not surprising; indeed, resistant mutants are expected to arise when any lifeform with the ability to rapidly reproduce and mutate is faced with a direct selective pressure, especially when a single drug is used against a single target. Staphylococci are frequently the cause of hospital infections such as infections from implanted medical devices. Many Staphylococci strains have become resistant to many modern day antibiotics. Improved therapies are needed.

One proposed strategy to overcome the problem of resistant variants is to indirectly attack bacteria by interfering with their means of communication, also known as quorum sensing. Targeting microbial communication makes sense because bacteria coordinate many of their virulence and pathogenesis pathways through these systems. Quave et al., report quorum sensing inhibitors of *Staphylococcus aureus* from botanical extracts. Planta Med. 2011, 77(02):188-95.

*Castanea sativa* (chestnut) is a flowering plant in the family Fagaceae which can be found in Europe. See Braga et al., Nat Prod Res., 2015, 29(1):1-18. Almeida et al. report in vivo skin irritation potential of a *Castanea sativa* (Chestnut) leaf extract. Basic & Clinical Pharmacol Toxicol, 2008, 103(5):461-7. See also Almeida et al. J Photochem Photobiol B: Biol, 2015, 144(0):28-34. Henry et al. report cosmetic compositions containing an extract of leaves of the *Castanea sativa* plant and cosmetic treatments. U.S. Pat. No. 8,067,044 (2011).

Garo et al., report asiatic acid and corosolic acid enhance the susceptibility of *Pseudomonas aeruginosa* biofilms to tobramycin. Antimicrob Agents Chemother, 2007, 51(5): 1813-7. See also Rangasamy et al. South African J Botany, 2014, 93:198-203.

Wong et al. report aqueous methanolic extracts of *Melastoma malabathricum* L. exhibited antibacterial activity. Nat Prod Res, 2012, 26(7):609-18

Perioni et al. report a survey on the natural ingredients used in folk cosmetics, cosmeceuticals and remedies for healing skin diseases. J Ethnopharmacol, 2004, 91(2-3):331-44.

References cited herein are not an admission of prior art.

SUMMARY

This disclosure relates to extracts from chestnut plants and compositions comprising one or more compounds contained therein and related uses reported herein. In certain embodiments, the extracts are derived from the leaves of a *Castanea* plant such as *Castanea sativa*.

In certain embodiments, the disclosure relates to extracts comprising a leaf derived mixture of compounds from a *Castanea* plant wherein the extracting process comprises one or more of the following steps of: mixing a leaf with methanol under conditions such that leaf compounds dissolves in the methanol and removing the methanol providing a methanol derived mixture of compounds; partitioning the methanol derived mixture of compounds in hexane and water providing a water derived mixture of compounds; partitioning the water derived mixture of compounds by mixing the water with ethyl acetate under conditions such that leaf compounds dissolve in the ethyl acetate and removing the ethyl acetate providing an ethyl acetate derived mixture of compounds; and purifying the ethyl acetate derived mixture of compounds by liquid chromatography through silica with a mobile phase comprising hexane and ethyl acetate; wherein the mobile phase comprises increasing amounts of ethyl acetate, and a mobile phase fraction is isolated comprising a leaf derived mixture of compounds which does not contain chlorogenic acid, ellagic acid, hyperoside, isoquercitrin, or rutin.

In certain embodiments, this disclosure relates to methods of treating or preventing a bacterial infections or acne comprising administering to a subject in need thereof or contacting the skin of a subject in need thereof with a formula comprising an extract or one or more compounds in an extract as disclosed herein. In certain embodiments, the formula is administered in combination with another antibiotic.

In certain embodiments, this disclosure relates to methods of treating or preventing a toxin-mediated bacterial infection comprising administering an effective amount of an *Castanea* extract or compounds contained therein to a subject in need thereof, including a subject at risk of, exhibiting symptoms of, or diagnosed with a *staphylococcal* scalded skin syndrome (esp. in neonates), abscesses, necrotizing fasciitis, sepsis, or atopic dermatitis (eczema).

In certain embodiments, the subject is at risk of, exhibiting symptoms of, or diagnosed with toxic shock syndrome, scalded skin syndrome, abscesses, furuncles, cellulitis, folliculitis, bloodstream infections, medical device infections, pneumonia, osteomyelitis, *staphylococcal* food poisoning, skin and soft tissue infections, endocarditis, eczema, atopic dermatitis, psoriasis, impetigo, septic arthritis, brain abscess, burn wounds, venous ulcers, diabetic foot ulcers, surgical wounds, post-operation infections, carbuncles, meningitis, bacteremia, necrotizing pneumonia, or necrotizing fasciitis.

In certain embodiments, the disclosure contemplates the use of an extract or one or more compounds in an extract disclosed herein in a tampon for the treatment or prevention of toxic shock syndrome.

In certain embodiments, the disclosure relates to a pharmaceutical or cosmetic formulation comprising an extract or one or more compounds in an extract disclosed herein and a pharmaceutically acceptable excipient or cosmetically acceptable excipient. In certain embodiments, the disclosure relates to a liquid or gel formulation optionally further comprising an antibacterial agent, a topical steroid, an anti-inflammatory agent, a promoter of skin barrier function, a skin moisturizer or combinations thereof. In certain embodiments the antibacterial agent is daptomycin, linezolid, vancomycin, nafcillin, cefazolin, dicloxacillin, clindamycin, rifampin, sulfamethoxale-trimethroprim (Bactrim), or botanical antibacterial agents, e.g., *Melaleuca alternifolia* tea tree oil.

In certain embodiments, the compound is in the form of an aqueous solution further comprising a buffering agent, oil, phosphate buffer, sodium or potassium salt, a saccharide, polysaccharide, or solubilizing agent.

Uses as an injectable product (for intravenous, intramuscular, subcutaneous, intradermal injections, intraperitoneal, or other administration) are contemplated. In certain embodiments, the disclosure relates to a pharmaceutical injectable formulation comprising an extract or one or more compounds in an extract disclosed herein and a pharmaceutically acceptable excipient. In certain embodiments, the disclosure relates to an injectable formulation optionally further comprising an antibacterial agent, a topical steroid, an anti-inflammatory agent, or combinations thereof. In certain embodiments the antibacterial agent is daptomycin, linezolid, vancomycin, nafcillin, cefazolin, dicloxacillin, clindamycin, rifampin, sulfamethoxale-trimethroprim (Bactrim), or botanical antibacterial agents, e.g., *Melaleuca alternifolia* tea tree oil.

In certain embodiments, the disclosure relates to a pharmaceutical composition comprising an extract or one or more compounds in an extract disclosed herein formulated with an enteric coating.

In certain embodiments, the disclosure relates to a solid or liquid soap or lotion comprising an extract or one or more compounds in an extract disclosed herein and a fatty acid.

In certain embodiments, the disclosure relates to a medical device comprising a coating comprising an extract or one or more compounds in an extract disclosed herein.

In certain embodiments, the disclosure relates to a tampon or tampon fibers comprising an extract or one or more compounds in an extract disclosed herein and an absorbent material.

In certain embodiments, the disclosure relates to a wound dressings or wound rinse comprising an extract or one or more compounds in an extract disclosed herein wherein the wound dressing comprises an absorbent pad and optionally an adhesive.

In certain embodiments, the disclosure relates to a disinfectant spray or wipe formulation for surfaces and fomites, comprising an extract and one or one or more compounds in an extract disclosed herein wherein the spray or wipe comprises an extract or one or more compounds in an extract disclosed herein such as a formula including chlorine based disinfectants.

DETAILED DISCUSSION

Figure 1:
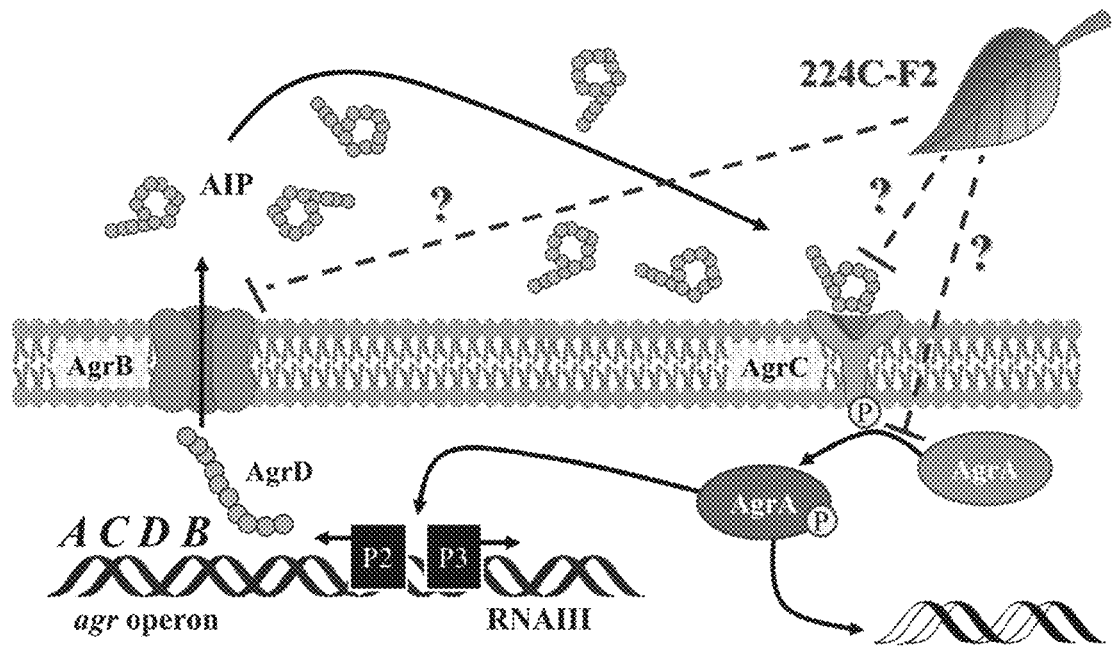
FIG. 1 illustrates a schematic of the *Staphylococcus aureus* accessory gene regulator system. The agr locus has been investigated in detail and is known to contain two divergent transcripts named RNAII and RNAIII The RNAII transcript is an operon of four genes, agrBDCA, that encode factors required to synthesize AIP and activate the regulatory cascade. Briefly, AgrD is the precursor peptide of AIP, AgrB is a membrane protease involved in generating AIP, AgrC is a histidine kinase that is activated by binding AIP, and AgrA is a response regulator that induces transcription of both RNAII and RNAIII. The RNAIII transcript yields a regulatory RNA molecule that acts as the primary effector of the agr system by up-regulating extracellular virulence factors and down-regulating cell surface proteins. The agr pathway is illustrated here with potential target sites for 224C-F2.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used herein, the term "combination with" when used to describe administration with an additional treatment means that the agent may be administered prior to, together with, or after the additional treatment, or a combination thereof.

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, "relative abundance" refers to amount determined from electrospray ionization mass spectrometry. Mass spectrometry is an analytical technique that can provide both qualitative (structure) and quantitative (molecular mass or concentration) information on analyte molecules after their conversion to ions. The molecules of interest are first introduced into the ionization source of the mass spectrometer, where they are first ionized to acquire positive or negative charges. The ions then travel through the mass analyzer and arrive at different parts of the detector according to their mass/charge (m/z) ratio. After the ions make contact with the detector, useable signals are generated and recorded by a computer system. The computer displays the signals graphically as a mass spectrum showing the relative abundance of the signals according to their m/z ratio.

Chestnut Leaf Extracts Block *Staphylococcus aureus* Virulence and Pathogenesis

Quorum quenching activity has been discovered in the natural products extracted from *Castanea sativa* leaves. The extract is able to attenuate virulence by quenching *S. aureus* agr-mediated quorum sensing, effectively blocking production of harmful exotoxins at sub-inhibitory concentrations for growth. Experiments indicate a lack of cytotoxicity to human skin cells, lack of growth inhibitory activity against the normal skin microflora, lack of resistance development, and efficacy in a skin abscess animal model.

*Staphylococcus aureus* is an abundant, opportunistic pathogen that is the causative agent of numerous infections. Due to its prevalence as a leading cause of healthcare-associated infection, and its highly multidrug resistant nature, *S. aureus* is a serious threat. It colonizes the nasal passages of approximately 30% of the healthy adult population. *S. aureus* infections initiate through trauma to the skin or mucosal layer and then progress through an invasive or toxin-mediated process. The prevalence of these infections has increased due to higher rates of immunosuppressive conditions, greater use of surgical implants, and dramatic increases in antibiotic resistance.

*S. aureus* produces an extensive array of enzymes, hemolysins, and toxins that are important to its ability to spread through tissues and cause disease. These virulence factors serve a wide scope of purposes in the infection process, including disruption of the epithelial barrier, inhibition of opsonization by antibody and complement, neutrophil cytolysis, interference with neutrophil chemotaxis, and inactivation of antimicrobial peptides. The expression of all of these invasive factors is controlled by cell-density quorum sensing using the autoinducing peptide (AIP) molecule. Like other quorum-sensing signals, AIP accumulates outside the cell until it reaches a critical concentration and then binds to a surface receptor called AgrC, initiating a regulatory cascade. Since AIP controls the expression of accessory factors for *S. aureus*, this regulatory system has been named the accessory gene regulator (agr), and the majority of the proteins necessary for this quorum-sensing system to function are encoded in the agr chromosomal locus. Applying inhibitors to quench this communication system to attenuate pathogenicity and virulence lies at the core of the quorum quenching approach.

Agr plays a key role in *S. aureus* pathogenesis. For example, skin and soft tissue infections are the most common type of infection caused by *S. aureus*. These range from minor inflammatory conditions to more invasive infection, and most of these cases are associated with the formation of abscesses, the hallmark of a *S. aureus* infection. The bulk of the phenotype is due to agr-dependent secreted virulence factors. Interference with the agr system through the use of competing AIPs or AIP-sequestering antibodies decreased abscess formation. These findings provide direct support for the notion that agr-targeted therapies could be an option for the development of skin infection treatments. Looking at other types of infections, agr mutants also display attenuated virulence in mice in the establishment of pneumonia and mortality, and in a systemic bloodstream infection model.

Given the importance of the agr system in pathogenesis, it has become the target of a number of chemical anti-virulence approaches. With the extracellular exposure of the AgrC receptor, chemists have developed receptor antagonists that successfully inhibit the system in vitro.

*Castanea sativa* leaves were identify as a potential source new anti-infective agents. Through design of a bioactivity-guided fractionation strategy based on limited growth-impact coupled to quorum sensing inhibition, a highly efficacious botanical composition with universal quenching activity was created for all agr alleles.

Figure 10:
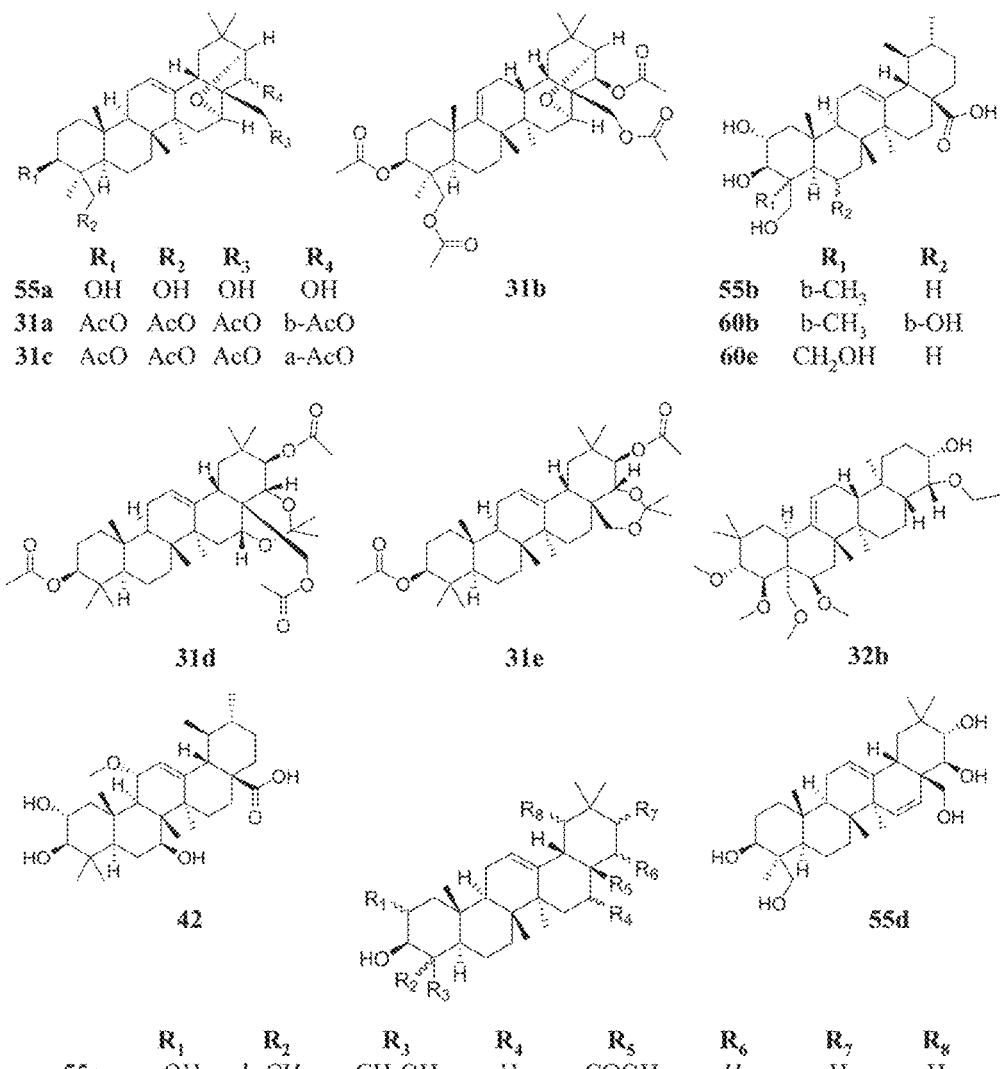
FIG. 10 illustrates putative structures of ursene and oleanene derivatives found in the most active region of 224C-F2 (retention time of 21-49 min) were determined following MS analysis and database searches. Compounds are listed by Peak number, corresponding to Table 4. Peak 31 was determined to be $C_{39}H_{59}O_8$ or $C_{38}H_{55}O_9$ with a relative abundance of 0.34%. Putative structural matches include: (31a) escigenin tetraacetate (6 CI); (31b) tetraacetate (7CI, 8CI) 16α, 21α-epoxy-olean-9(11)-ene-3β,22β,24,28-tetrol; (31c) tetraacetate aescigenin; (31d) triacetate (8CI) cyclic 16,22-acetal-olean-12-ene-3β,16α,21β,22α,28-pentol;
(31e) triacetate (8CI) cyclic 22, 28-acetal-olean-12-ene-3β, 16α,21β,22α,28-pentol. Peak 32 was determined to be $C_{35}H_{59}O_6$ with a relative abundance of 0.30%. Putative structural matches include: (32a) stigmastane (FIG. 11) and (32b) (3β,4β,16α,21β,22α)-16,21,22,23,28-pentamethoxy (9CI) olean-12-en-3-ol. Peak 42 was determined to be $C_{31}H_{49}O_6$ with a relative abundance of 1.43%. Putative structural matches included (42) amirinic acid. Peak 52 was determined to be $C_{32}H_{51}O_7$ with a relative abundance of 0.48%. Putative structural matches include: (52a) 21-acetate protoescigenin, (52b) 16-acetate protoescigenin, (52c) 22-acetate protoescigenin and (52d) 28-acetate protoescigenin. Peak 55 was determined to be $C_{30}H_{48}O_5$, with a relative abundance of 4.11%. Putative structural matches include: (55a) 16,21-epoxy-(3β,4β,16α,21α,22β-olean-12-ene-3,22,24,28-tetrol (9CI); (55b) asiatic acid; (55c) arjunolic acid; (55d) isoescigenin. Peak 60 was determined to be $C_{30}H_{48}O_6$, with a relative abundance of 6.80%. Putative structural matches include: (60a) camelliagenin E; (60b) brahmic acid; (60c) sericic acid; (60d) belleric acid; and (60e) 2,3,23,24-tetrahydroxy-(2α,3β)-urs-12-en-28-oic acid. Peak 64 was determined to be $C_{30}H_{45}O_5$, with a relative abundance of 2.91%. The putative structural match is (64) ouillaic acid.

Reported herein are quorum quenching effects of a botanical composition rich in ursene and oleanene derivatives (FIG. 10) against *S. aureus*. Additional compounds identified in the most active region (at <1% relative abundance each) included putative gallotannins, which share a trigalloyl structure with varying core sugars, and a putative ellagitannin.

Figure 6A:
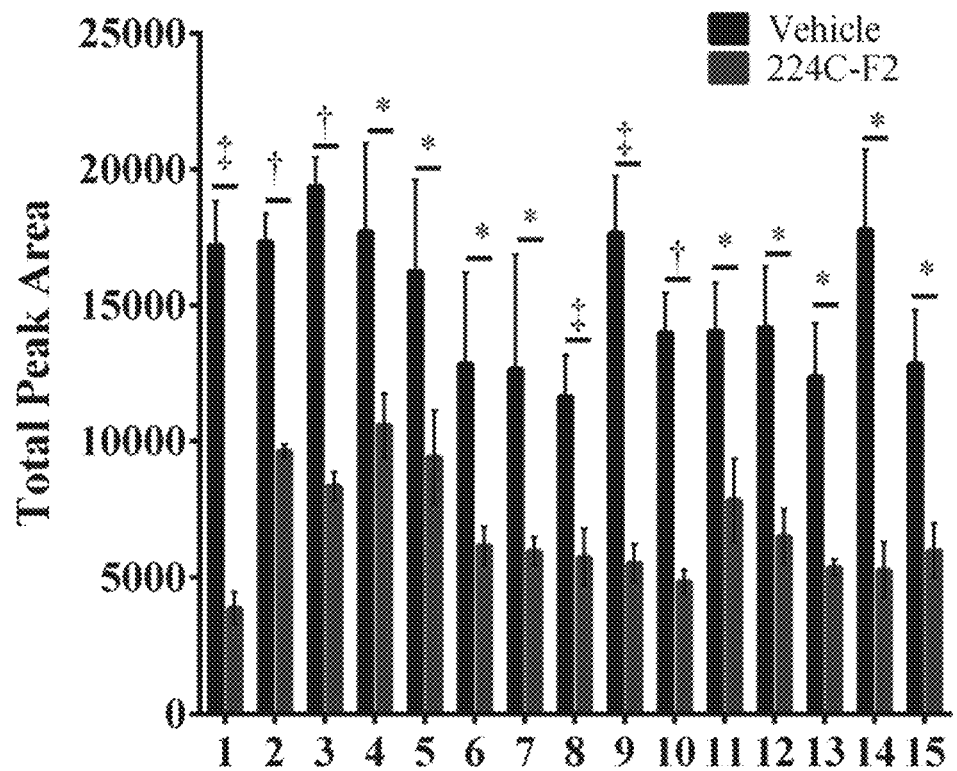
FIG. 6A shows data indicating 224C-F2 attenuates virulence without any detectable resistance after 15 days of drug passaging. Cultures of USA500 isolate NRS385 (agr group I) were passaged for 15 consecutive days in the presence of 16 µg mL$^{-1}$ of 224C-F2. The sum total peak area of de-formylated and formylated delta toxin was quantified for the mock vehicle control (DMSO) and treated group. A significant difference ($p<0.05$) was evident for all treatment days.
Figure 6B:
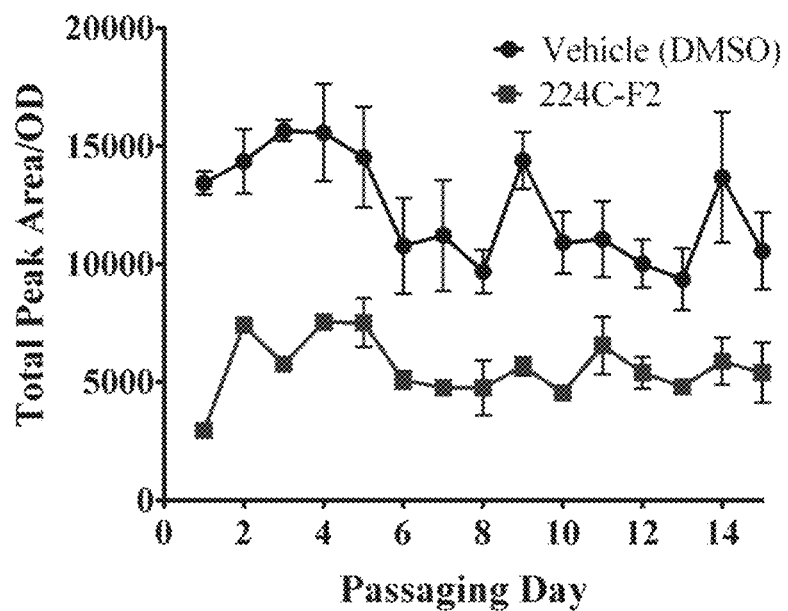
FIG. 6B shows data indicating 224C-F2 inhibited delta-toxin production over the length of the passaging experiment in the absence of growth inhibition.

Safety studies in both human keratocytes (HaCaT cells) and murine skin (FIG. 6) have confirmed that this version of chestnut leaf extract (224C-F2) can be considered safe for topical applications based on its lack of cytotoxic and irritant effects.

Several layers of evidence in support of the efficacy of *C. sativa* leaf extracts in blocking *S. aureus* virulence have been presented. Specifically, chestnut leaf extracts are effective in blocking production of the translational products of RNAIII, including a number of exotoxins. Overall virulence was quenched as demonstrated by the lack of cytotoxic effects elicited by supernatants of cultures treated with the extract. Importantly, using an in vivo model, efficacy in attenuating dermonecrosis was demonstrated, even in the absence of adjuvant antibiotics.

This inhibition of virulence and pathogenesis was accomplished without posing growth inhibitory pressures on not only *S. aureus*, but also a panel of common members of the human cutaneous microbiome. A robust skin microflora is critical to skin barrier health and prevention of disease onset. The majority of the bacterial cutaneous microbiome is represented by Actinobacteria, Firmicutes, Proteobacteria and Bacteroidetes. Much like cases of dysbiosis in gut microflora, broad-spectrum activity against the skin microflora also holds the potential for fostering an environment amenable to the proliferation of pathogenic bacteria. The presence of commensals, like *Staphylococcus epidermidis*, is essential to the state of host innate immunity. Thus, it is noteworthy that 224C-F2 specifically blocks *S. aureus* virulence without adding selective pressures on major representatives of the cutaneous microbiome.

Multiple lines of evidence suggest that components within 224C-F2 directly target the core machinery of the agr system, such as the observation of agr P3 promoter reduction (FIG. 3) and reduced levels of δ-toxin production (FIG. 4), which is encoded within RNAIII transcript regulated by P3. If 224C-F2 only targeted downstream factors regulated by quorum sensing, such as α-hemolysin, inhibition of agr P3 or δ-toxin production would not have been expected. Potential targets within the agr system include inhibition of AIP docking with AgrC, prevention of AIP production through AgrB, or reduction of AgrA activation (FIG. 1).

Following 15 days of sequential passaging with 224C-F2 in vitro, no resistance was detected. Thus, it is contemplated that 224C-F2 and compounds contained therein are a therapeutic option due to its ability to specifically target and quench *S. aureus* virulence. Importantly, this composition was non-toxic to human keratinocytes and no dermatopathology was noted upon administration to murine skin. Moreover, the composition did not inhibit growth of the normal skin microflora, suggesting that its disruptive action on the cutaneous microbiome would be minimal.

One major benefit of using virulence inhibitors with a classical antibiotic is the potential for increased antibiotic efficacy. By blocking the toxins responsible for immune response damage, the antibiotics and immune system can work more in concert to eliminate the bacteria.

Other topical formulations for skin flares (i.e. for atopic dermatitis or other infections related to a disrupted skin barrier) that may be combined with the anti-virulence drug include: topical steroids, anti-inflammatory agents, and promoters of skin barrier function or skin moisturizers such as ceramide, glycerin, colloidal oatmeal.

In certain embodiments the disclosure contemplates that an extract or one or more compounds in an extract disclosed herein may be used as a virulence inhibitor applications optionally in combination with other antibacterial agents for prevention of disease onset and treatment such as in medical device coatings (medical implants and tools, IV catheters), wound dressings (embedded in gauze bandages), wound rinses (i.e. surgical rinses), wound-vacuum systems, whole body baths (e.g., in combo with bleach baths for treatment of skin flares for atopic dermatitis/eczema), soaps, personal care products (body washes, lotions, soaps) for high risk patients or for populations with high risk of exposure (e.g. athletes using common sports equipment in gym) human and veterinary applications (e.g. anti-infectives for companion animals, race horses, etc.)

Methods of Use

In certain embodiments, this disclosure relates to methods of treating or preventing a bacterial infections comprising administering or contacting a formula comprising an extract or one or more compounds in an extract as disclosed herein to a subject in need thereof. In certain embodiments, the formula is administered in combination with another antibiotic agent.

In further embodiments, the subject is co-administered with an antibiotic selected from the group comprising of sulfonamides, diaminopyrimidines, quinolones, beta-lactam antibiotics, cephalosporins, tetracyclines, notribenzene derivatives, aminoglycosides, macrolide antibiotics, polypeptide antibiotics, nitrofuran derivatives, nitroimidazoles, nicotinin acid derivatives, polyene antibiotics, imidazole derivatives or glycopeptide, cyclic lipopeptides, glycylcyclines and oxazolidinones. In further embodiments, these antibiotics include but are not limited to sulphadiazine, sulfones—[dapsone (DDS) and paraaminosalicyclic (PAS)], sulfanilamide, sulfamethizole, sulfamethoxazole, sulfapyridine, trimethoprim, pyrimethamine, nalidixic acids, norfloxacin, ciproflaxin, cinoxacin, enoxacin, gatifloxacin, gemifloxacin, grepafloxacin, levofloxacin, lomefloxacin, moxifloxacin, ofloxacin, pefloxacin, sparfloxacin, trovafloxacin, penicillins (amoxicillin, ampicillin, azlocillin, carbenicillin, cloxacillin, dicloxacillin, flucloxacillin, hetacillin, oxacillin, mezlocillin, penicillin G, penicillin V, piperacillin), cephalosporins (cefacetrile, cefadroxil, cefalexin, cefaloglycin, cefalonium, cefaloridin, cefalotin, cefapirin, cefatrizine, cefazaflur, cefazedone, cefazolin, cefradine, cefroxadine, ceftezole, cefaclor, cefonicid, ceforanide, cefprozil, cefuroxime, cefuzonam, cefmetazole, cefoteta, cefoxitin, cefcapene, cefdaloxime, cefdinir, cefditoren, cefetamet, cefixime, cefmenoxime, cefodizime, cefoperazone, cefotaxime, cefotiam, cefpimizolecefpiramide, cefpodoxime, cefteram, ceftibuten, ceftiofur, ceftiolen, ceftizoxime, ceftriaxone, cefoperazone, ceftazidime, cefepime), moxolactam, carbapenems (imipenem, ertapenem, meropenem) monobactams (aztreonam)oxytetracycline, chlortetracycline, clomocycline, demeclocycline, tetracycline, doxycycline, lymecycline, meclocycline, methacycline, minocycline, rolitetracycline, chloramphenicol, amikacin, gentamicin, framycetin, kanamycin, neomycin, netilmicin, streptomycin, tobramycin, azithromycin, clarithromycin, dirithromycin, erythromycin, roxithromycin, telithromycin, colistin, bacitracin, tyrothricin, notrifurantoin, furazolidone, metronidazole, tinidazole, isoniazid, pyrazinamide, ethionamide, nystatin, amphotericin-B, hamycin, miconazole, clotrimazole, ketoconazole, fluconazole, rifampacin, lincomycin, clindamycin, spectinomycin, fosfomycin, loracarbef, polymyxin B, polymyxin B Sulfate, procain, ramoplanin, teicoplanin, vancomycin, and/or nitrofurantoin.

In certain embodiments, this disclosure relates to methods of treating or preventing a toxin-mediated bacterial infection comprising administering an effective amount of a *Castanea* extract or compounds contained therein to a subject in need thereof, including a subject at risk of, exhibiting symptoms of, or diagnosed with a *staphylococcal* scalded skin syndrome (esp. in neonates), abscesses, necrotizing fasciitis, sepsis, atopic dermatitis (eczema) and more.

In certain embodiments, the subject is at risk of, exhibiting symptoms of, or diagnosed with toxic shock syndrome, scalded skin syndrome, abscesses, furuncles, cellulitis, folliculitis, bloodstream infections, medical device infections, pneumonia, osteomyelitis, *staphylococcal* food poisoning, skin and soft tissue infections, endocarditis, eczema, atopic dermatitis, psoriasis, impetigo, septic arthritis, brain abscess, burn wounds, venous ulcers, diabetic foot ulcers, surgical wounds, post-operation infections, carbuncles, meningitis, bacteremia, necrotizing pneumonia, or necrotizing fasciitis.

In certain embodiments, the disclosure contemplates methods of preventing bacterial infections by applying extracts or one or more compounds in extracts disclosed herein in a tampon for prevention against adverse effects associated with vaginal area infections and possibly bladder infections, e.g., toxic shock syndrome. As used herein a "tampon" refers to device containing an absorbent material, configured to be inserted into a vagina to absorb menstrual flow and typically expand during use, typically in the shape of a cylinder. Tampons may expand axially (increase in length), while digital tampons will expand radially (increase in diameter). Most tampons have a cord or string for removal. Typical tampon materials include cloth, fibers, cotton, or rayon, or a blend of rayon and cotton.

Bacterial toxins may cause toxic shock syndrome (TSS). Enterotoxin type B or TS ST-1 of *Staphylococcus aureus* are believed to cause TSS. Streptococcal TSS is sometimes referred to as toxic shock-like syndrome (TSLS) or streptococcal toxic shock syndrome (STSS). CDC criteria for diagnosing *staphylococcal* toxic shock syndrome is based on 1) a body temperature of greater than 38.9° C. (102.02° F.) 2) a Systolic blood pressure of greater than 90 mmHg 3) diffuse macular erythroderma 4) desquamation (especially of the palms and soles) 1-2 weeks after onset 5) involvement of three or more organ systems: gastrointestinal (vomiting, diarrhea), muscular: severe myalgia or creatine phosphokinase level at least twice the upper limit of normal for laboratory, mucous membrane hyperemia (vaginal, oral, conjunctival), kidney failure (serum creatinine>2 times normal), liver inflammation (bilirubin, AST, or ALT>2 times normal), low platelet count (platelet count<100,000/mm$^3$), Central nervous system involvement (confusion without any focal neurological findings) and 6) Negative results of: blood, throat, and CSF cultures for other bacteria (besides *S. aureus*) negative serology for Rickettsia infection, leptospirosis, and measles. Cases are classified as probable is five of the six criteria above are met.

In certain embodiments, the disclosure contemplates methods of preventing general transmission of bacterial through use of extracts and one or more compounds in an extract disclosed herein as a general agent formulated into a spray or wipe product, paper or fiber based cloth. For example, one can use such a product to treat athletic equipment (football pads, bench presses, gym surfaces), where invasive toxin mediated staph often lurks and causes infections in healthy people through toxin production.

In certain embodiments, the disclosure relates to methods of treating acne comprising administering an effective amount of a composition comprising an extract or one or more compounds in an extract as disclosed herein to a subject at risk of, exhibiting symptoms of, or diagnosed with acne, blackheads, papules, pustules or nodules. In certain embodiments, the subject is undergoing puberty, between 10 and 20 years of age. In certain embodiments, the subject is a female, and the composition is administered within seven days of the beginning of a menstrual cycle. Administration may be by topical application through hand or by spray of a liquid or lotion containing an extract or one or more compounds in an extract disclosed herein.

Extracts and Compounds

In certain embodiments, an extract is made by the process of extracting a mixture of compounds from the leaves, roots, bark, stem, or branches of a *Castanea* plant e.g., *Castanea sativa*. Other contemplated plants include: *Castanea acuminatissima, Castanea alabamensis, Castanea alnifolia, Castanea americana, Castanea argentea, Castanea argyrophylla, Castanea arkansana, Castanea armata, Castanea ashei, Castanea blaringhemii, Castanea bodinieri, Castanea brevicuspis, Castanea bungeana, Castanea burbankii, Castanea buruana, Castanea californica, Castanea Castanea, Castanea castanicarpa, Castanea castenea var. pubinervis, Castanea chincapin, Castanea chinensis, Castanea chrysophylla, Castanea concinna, Castanea cooperta, Castanea costata, Castanea coudersii, Castanea crenata, Castanea davidii, Castanea dentata, Castanea diversifolia, Castanea dovaricata, Castanea duclouxii, Castanea echidnocarpa, Castanea edonii, Castanea edwii, Castanea endicottii, Castanea eonii, Castanea fagus, Castanea falconeri, Castanea fargesii, Castanea fauriei, Castanea fleetii, Castanea floridana, Castanea formosana, Castanea furfurella, Castanea glomerata, Castanea henryi, Castanea henryi, Castanea hupehensis, Castanea hystrix, Castanea, Castanea inermis, Castanea japonica, Castanea javanica, Castanea kusakuri, Castanea lanceifolia, Castanea latifolia, Castanea margaretta, Castanea martabanica, Castanea microcarpa, Castanea mollissima, Castanea montana, Castanea morrisii, Castanea nana, Castanea neglecta, Castanea ozarkensis, Castanea paucispina, Castanea phansipanensis, Castanea prolifera, Castanea pubinervis, Castanea pulchella, Castanea pumila, Castanea purpurella, Castanea regia, Castanea rhamnifolia, Castanea rockii, Castanea roxburghii, Castanea seguinii, Castanea sempervirens, Castanea sessilifolia, Castanea sinensis, Castanea sloanea, Castanea spectabilis, Castanea sphaeroarpa, Castanea sphaerocarpa, Castanea stricta, Castanea sumatrana, Castanea tribuloides, Castanea tungurrut, Castanea vesca, Castanea vilmoriniana, Castanea vulgaris, Castanea wattii* and hybrids thereof.

In certain embodiments, the extracting process comprises the step of mixing the leaf from the plant with a polar solvent, such as a liquid comprising methanol, ethanol, ethyl acetate, acetonitrile, acetone, methylene chloride or chloroform, under conditions such that a mixture of compounds in the leaf dissolves in the solvent. In certain embodiments, the process further comprises the step of removing the solvent by evaporation from the mixture of compounds. In certain embodiments, the process further comprises the step of purifying the mixture of compounds by liquid chromatography through a solid absorbent, e.g., wherein the solid absorbent comprises silica gel or alumina.

In certain embodiments, the disclosure relates to extracts comprising a leaf derived mixture of compounds from a *Castanea* plant wherein the extracting process comprises the steps of: mixing a leaf with methanol under conditions such that leaf compounds dissolves in the methanol and removing the methanol providing a methanol derived mixture of compounds; partitioning the methanol derived mixture of compounds in hexane and water providing a water derived mixture of compounds; partitioning the water derived mixture of compounds by mixing the water with ethyl acetate under conditions such that leaf compounds dissolve in the ethyl acetate and removing the ethyl acetate providing an ethyl acetate derived mixture of compounds; and purifying the ethyl acetate derived mixture of compounds by liquid chromatography through silica with a mobile phase comprising hexane and ethylene acetate; wherein the mobile phase comprises increasing amounts of ethyl acetate, and a mobile phase fraction is isolated comprising a leaf derived mixture of compounds which does not contain chlorogenic acid, ellagic acid, hyperoside, isoquercitrin, or rutin.

Chromatography refers to the separation of a mixture of compounds dissolved in a fluid called the mobile phase, which carries the compounds through a structure holding another material called the stationary phase. The various compounds or components of the mixture travel at different speeds, causing them to separate. The separation is based on differential partitioning between the mobile and stationary phases. Subtle differences in a partition coefficient of each compound result in differential retention on the stationary phase and thus changing the separation.

In normal-phase chromatography, the stationary phase is polar. In reversed phase, the stationary phase is nonpolar. Typical stationary phases for normal-phase chromatography are silica or organic moieties with cyano and amino functional groups. For reversed phase, alkyl hydrocarbons are the preferred stationary phase. Examples are solid supports containing a surface conjugated with a hydrocarbon chain, e.g., octadecyl (C18), octyl (C8), and butyl (C4).

In normal-phase chromatography, the least polar compounds elute first and the most polar compounds elute last. The mobile phase typically consists of a nonpolar solvent such as hexane or heptane mixed with a slightly more polar solvent such as isopropanol, ethyl acetate or chloroform. Retention to the stationary phase decreases as the amount of polar solvent in the mobile phase increases. In reversed phase chromatography, the most polar compounds elute first with the most nonpolar compounds eluting last. The mobile phase is generally a binary mixture of water and a miscible polar organic solvent like methanol, acetonitrile or THF.

In certain embodiments, methods of extraction comprise mixing leaves of a *Castanea* plant with an water miscible carbon containing solvent, e.g., such as a protic solvent, an alcohol, methanol, ethanol, 1-propanol, 2-propanol, tetrahydrofuran, acetone, acetic acid, 1,4-dioxane or mixture providing a concentrate with a mixture of compounds and substantially removing the solvent from the concentrate, purifying the solvent derived concentrate to less than 5%, 1%, or 0.5% by weight of the solvent used in the extraction, e.g., evaporating the protic solvent and/or optionally in combination with mixing the concentrate with water, sonicating the water, freezing the water to provide ice, and removing the ice by sublimation (e.g. in a vacuum of low pressure) wherein said purification methods may be repeated in combination. In certain embodiments, the method further comprises suspending the solvent derived concentrate in water and optionally extract impurities in a hydrocarbon solvent such as cyclohexane, heptane, hexane, pentane, 2,2,4-trimethylpentane, separating the hydrocarbon from the water providing a water layer. In certain embodiments, the method further comprises mixing the water layer with a solvent that is immiscible in water (polar and/or aprotic), e.g., such as ethyl acetate, diethyl ether, methyl tertbutyl ether, toluene, methylene chloride, carbon tetrachloride, 1,2-di chl oroethant, and/or chloroform, and purifying the solvent to provide a second solvent derived concentrate. In further embodiments, the second derived concentrate is purified one or more times by liquid chromatography, e.g., normal phase chromatography. Typically the solid absorbent is polar such as silica. In certain embodiments, the extract is a portion isolated after the column solvent is more than 50% ethyl acetate in hexane.

In certain embodiments, the mixture of compounds comprises components of the following formulas and relative abundance $C_{57}H_{24}O_2$ (2.67%), $C_{27}H_{50}O_6$ (2.65%), $C_{31}H_{50}O_6$ (1.43%), $C_{30}H_{46}O_7$ (1.86%), and two compounds $C_{57}H_{23}O_2N_3$ (1.64% and 3.13%, respectively), two compounds $C_{59}H_{25}O_3$ (1.45 and 1.07%, respectively), $C_{41}H_{33}O_{16}$ (1.20%) and $C_{30}H_{47}O_5$ (5.96%).

In certain embodiments, the mixture of compounds comprises components having the following formulas and relative abundance, $C_{39}H_{59}O_8$ or $C_{38}H_{55}O_9$, or mixture, with a relative abundance of 0.1 to 0.9%, e.g. 0.3%; $C_{35}H_{59}O_6$ with a relative abundance of 0.1 to 0.9%, e.g., 0.3%; $C_{31}H_{49}O_6$ with a relative abundance of 1.0 to 2.0%, e.g., 1.4%; $C_{32}H_{51}O_7$ with a relative abundance of 0.1 to 0.9%, e.g., 0.5%; $C_{30}H_{48}O_6$ with a relative abundance of 3.0 to 5.0%, e.g., 4.1%; $C_{30}H_{48}O_6$ with a relative abundance of 6.0 to 8.0%, e.g., 6.8%; and $C_{30}H_{45}O_5$ with a relative abundance of 2.0 to 4.0%, e.g., 2.9%. Typically the mixture further comprises additional components of different compounds having the following formula and relative abundance, $C_{35}H_{59}O_6$ with a relative abundance of 0.2 to 0.4, e.g., 0.30%; $C_{27}H_{23}O_{18}$ with a relative abundance of 0.05 to 0.30, e.g., 0.16%; $C_{39}H_{31}O_{15}$ with a relative abundance of 0.50 to 0.80, e.g., 0.65%; $C_{17}H_{11}O_8$ or $C_{20}H_{11}O_4N_2$, or mixture, with a relative abundance of 0.5 to 1.0, e.g., 0.7%; and $C_{34}H_{29}O_{15}$ with a relative abundance of 0.2 to 0.4%, e.g., 0.3%.

In certain embodiment, the extract comprises at mixture comprises at least one component from each of the following groups a) to g): a) a compound selected from escigenin tetraacetate (6CI); tetraacetate (7CI,8CI) 16α,21α-epoxy-olean-9(11)-ene-3β,22β,24,28-tetrol; tetraacetate aescigenin; triacetate (8CI) cyclic 16,22-acetal-olean-12-ene-3β, 16α,21β,22α,28-pentol; and triacetate (8CI) cyclic 22,28-acetal-olean-12-ene-3β,16α,21β,22α,28-pentol, or mixture of two, three, four or all; b) a compound selected from stigmastane and (3β,4β,16α,21β,22α)-16,21,22,23,28-pentamethoxy (9CI) olean-12-en-3-ol, or mixture; c) amirinic acid; d) a compound selected from 21-acetate protoescigenin, 16-acetate protoescigenin, 22-acetate protoescigenin and 28-acetate protoescigenin, or mixture of two, three, four or all;

e) a compound selected from 16,21-epoxy-(3β,4β,16α, 21α,22β)-olean-12-ene-3,22,24,28-tetrol (9CI); asiatic acid; arjunolic acid; and isoescigenin, or mixture of two, three, or all;

f) a compound selected from camelliagenin E; brahmic acid; sericic acid; belleric acid; and 2,3,23,24-tetrahydroxy-(2α,3β)-urs-12-en-28-oic acid, or mixture of two, three, four or all; and g) ouillaic acid. Typically, the mixture further comprises at least one component from each of the following groups a) to d): a) a compound selected from stigmastane and (3β,4β, 16α,21β,22α)-16,21,22,23,28-pentamethoxy (9CI) olean-12-en-3-ol or a mixture; b) a compound selected from 1,3,6-tri-O-galloylglucose; 1,2,6-tri-galloyl-β-D-glucose; 1,2,3-tri-O-galloylglucose; 1,2,3-tri-O-galloyl-β-D-glucopyranose; 2',3,5-tri-O-galloyl-D-hamamelose; 2-C-[[(3,4, 5-trihydroxybenzoyl)oxy]methyl]-1,5-bis(3,4,5-trihydroxybenzoate) D-ribofuranose; kurigalin; and 3,4,6-tri-O-galloyl-D-glucose, or mixture of two, three, four, five, six, seven, or all; c) castanoside B; and d) a compound selected from 3,4,3'-tri-O-methylellagic acid and 3,3',4'-tri-O-methylellagic acid, or a mixture.

Pharmaceutical Formulation

In certain embodiments, the disclosure relates to a pharmaceutical formulation comprising an extract or one or more compounds in an extract disclosed herein and a pharmaceutically acceptable excipient or additive. In certain embodiments, the disclosure relates to a lotion, liquid, or gel formulation optionally further comprising an antibiotic agent, a topical steroid, an anti-inflammatory agent, a promoter of skin barrier function, a skin moisturizer or combinations thereof.

Examples of antibiotics include but are not limited to sulphadiazine, sulfones—[dapsone (DDS) and paraaminosalicyclic (PAS)], sulfanilamide, sulfamethizole, sulfamethoxazole, sulfapyridine, trimethoprim, pyrimethamine, nalidixic acids, norfloxacin, ciproflaxin, cinoxacin, enoxacin, gatifloxacin, gemifloxacin, grepafloxacin, levofloxacin, lomefloxacin, moxifloxacin, ofloxacin, pefloxacin, sparfloxacin, trovafloxacin, penicillins (amoxicillin, ampicillin, azlocillin, carbenicillin, cloxacillin, dicloxacillin, flucloxacillin, hetacillin, oxacillin, mezlocillin, penicillin G, penicillin V, piperacillin), cephalosporins (cefacetrile, cefadroxil, cefalexin, cefaloglycin, cefalonium, cefaloridin, cefalotin, cefapirin, cefatrizine, cefazaflur, cefazedone, cefazolin, cefradine, cefroxadine, ceftezole, cefaclor, cefonicid, ceforanide, cefprozil, cefuroxime, cefuzonam, cefmetazole, cefoteta, cefoxitin, cefcapene, cefdaloxime, cefdinir, cefditoren, cefetamet, cefixime, cefmenoxime, cefodizime, cefoperazone, cefotaxime, cefotiam, cefpimizolecefpiramide, cefpodoxime, cefteram, ceftibuten, ceftiofur, ceftiolen, ceftizoxime, ceftriaxone, cefoperazone, ceftazidime, cefepime), moxolactam, carbapenems (imipenem, ertapenem, meropenem) monobactams (aztreonam)oxytetracycline, chlortetracycline, clomocycline, demeclocycline, tetracycline, doxycycline, lymecycline, meclocycline, methacycline, minocycline, rolitetracycline, chloramphenicol, amikacin, gentamicin, framycetin, kanamycin, neomycin, netilmicin, streptomycin, tobramycin, azithromycin, clarithromycin, dirithromycin, erythromycin, roxithromycin, telithromycin, colistin, bacitracin, tyrothricin, notrifurantoin, furazolidone, metronidazole, tinidazole, isoniazid, pyrazinamide, ethionamide, nystatin, amphotericin-B, hamycin, miconazole, clotrimazole, ketoconazole, fluconazole, rifampacin, lincomycin, clindamycin, spectinomycin, fosfomycin, loracarbef, polymyxin B, polymyxin B Sulfate, procain, ramoplanin, teicoplanin, vancomycin, and/or nitrofurantoin.

Examples of steroids include hydrocortisone, hydrocortisone valerate, hydrocortisone 17-butyrate, mometasone, mometasone furoate, halobetasol propionate, desonide, desoximetasone, fluocinolone acetonide, alclometasone dipropionate, flurandrenolide, fluticasone propionate, diflucortolone, diflucortolone valerate, diflorasone diacetate, clobetasol, clobetasone butyrate, clobetasol propionate, betamethasone dipropionate, betamethasone valerate, beclomethasone, budesonide, flunisolide, fluocinonide, triamcinolone, triamcinolone acetonide, methylprednisolone, methylprednisolone aceponate, prednicarbate, prednisolone, and prednisone and alternate salts thereof. Examples of contemplated anti-inflammatory agents are aspirin, celecoxib, diclofenac, diflunisal, etodolac, ibuprofen, indomethacin, ketoprofen, naproxen, oxaprozin, and piroxicam.

In certain embodiments, the disclosure relates to a pharmaceutical composition comprising an extract or one or more compounds in an extract disclosed herein formulated with an enteric coating. In certain embodiments, the disclosure relates to a pharmaceutical formulation of an extract or one or more compounds in an extract disclosed herein which protect the compositions from the acidity and enzymatic action of gastric secretions. In certain embodiments, the pharmaceutical formulations contain an extract or one or more compounds in an extract disclosed herein in a composition with an enteric coating along with another pharmaceutically acceptable vehicle. In certain embodiments, compositions comprising an extract or one or more compounds in an extract disclosed herein may be directly-compressible without excipients, into a tablet of pharmaceutically acceptable hardness, e.g., compressed into a tablet, optionally with a lubricant, such as but not limited to magnesium stearate, and enteric coated. In another embodiment, the pharmaceutical compositions containing an extract or one or more compounds in an extract disclosed herein alternatively include one or more substances that either neutralize stomach acid and/or enzymes or are active to prevent secretion of stomach acid.

The pharmaceutical composition can be formulated for oral administration as, for example but not limited to, drug powders, crystals, granules, small particles (which include particles sized on the order of micrometers, such as microspheres and microcapsules), particles (which include particles sized on the order of millimeters), beads, microbeads, pellets, pills, microtablets, compressed tablets or tablet triturates, molded tablets or tablet triturates, and in capsules, which are either hard or soft and contain the composition as a powder, particle, bead, solution or suspension. The pharmaceutical composition can also be formulated for oral administration as a solution or suspension in an aqueous liquid, as a liquid incorporated into a gel capsule or as any other convenient formulation for administration, or for rectal administration, as a suppository, enema or other convenient form.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

Suitably, the pharmaceutical composition of the disclosure comprises a carrier and/or diluent appropriate for its delivering by injection to a human or animal organism. Such carrier and/or diluent is non-toxic at the dosage and concentration employed. It is selected from those usually employed to formulate compositions for parental administration in either unit dosage or multi-dose form or for direct infusion by continuous or periodic infusion. It is typically isotonic, hypotonic or weakly hypertonic and has a relatively low ionic strength, such as provided by sugars, polyalcohols and isotonic saline solutions. Representative examples include sterile water, physiological saline (e.g. sodium chloride), bacteriostatic water, Ringer's solution, glucose or saccharose solutions, Hank's solution, and other aqueous physiologically balanced salt solutions. The pH of the composition of the disclosure is suitably adjusted and buffered in order to be appropriate for use in humans or animals, typically at a physiological or slightly basic pH (between about pH 8 to about pH 9, with a special preference for pH 8.5). Suitable buffers include phosphate buffer (e.g. PBS), bicarbonate buffer and/or Tris buffer. A typical composition is formulated in 1M saccharose, 150 mM NaCl, 1 mM $MgCl_2$, 54 mg/l Tween 80, 10 mM Tris pH 8.5. Another typical composition is formulated in 10 mg/ml mannitol, 1 mg/ml HSA, 20 mM Tris, pH 7.2, and 150 mM NaCl.

The pharmaceutical formulation can also include any type of pharmaceutically acceptable excipients, additives or vehicles. For example, but not by way of limitation, diluents or fillers, such as dextrates, dicalcium phosphate, calcium sulfate, lactose, cellulose, kaolin, mannitol, sodium chloride, dry starch, sorbitol, sucrose, inositol, powdered sugar, bentonite, microcrystalline cellulose, or hydroxypropylmethylcellulose may be added to the composition comprising an extract or one or more compounds in an extract disclosed herein to increase the bulk of the composition. Also, binders, such as but not limited to, starch, gelatin, sucrose, glucose, dextrose, molasses, lactose, acacia gum, sodium alginate, extract of Irish moss, panwar gum, ghatti gum, mucilage of isapgol husks, carboxymethylcellulose, methylcellulose, polyvinylpyrrolidone, Veegum and starch arabogalactan, polyethylene glycol, ethylcellulose, and waxes, may be added to the formulation to increase its cohesive qualities. Additionally, lubricants, such as but not limited to, talc, magnesium stearate, calcium stearate, stearic acid, hydrogenated vegetable oils, polyethylene glycol, sodium benzoate, sodium acetate, sodium chloride, leucine, carbowax, sodium lauryl sulfate, and magnesium lauryl sulfate may be added to the formulation. Also, glidants, such as but not limited to, colloidal silicon dioxide or talc may be added to improve the flow characteristics of a powdered formulation. Finally, disintegrants, such as but not limited to, starches, clays, celluloses, algins, gums, crosslinked polymers (e.g., croscarmelose, crospovidone, and sodium starch glycolate), Veegum, methylcellulose, agar, bentonite, cellulose and wood products, natural sponge, cation-exchange resins, alginic acid, guar gum, citrus pulp, carboxymethylcellulose, or sodium lauryl sulfate with starch may also be added to facilitate disintegration of the formulation in the intestine.

In certain embodiments, the formulation contains a directly compressible composition comprising an extract or one or more compounds in an extract disclosed herein but no excipients, additives or vehicles other than an enteric coating; however, the formulation may contain a lubricant, such as but not limited to, magnesium stearate. Preferably, the directly compressed formulation is formulated as a tablet of pharmaceutically acceptable hardness (greater than 6 kp, preferably 8-14 kp, and more preferably 10-13 kp).

Polymers which are useful for the preparation of enteric coatings include, but are not limited to, shellac, starch and amylose acetate phthalates, styrene-maleic acid copolymers, cellulose acetate succinate, cellulose acetate phthalate (CAP), polyvinylacetate phthalate (PVAP), hydroxypropylmethylcellulose phthalate (grades HP-50 and HP-55), ethylcellulose, fats, butyl stearate, and methacrylic acid-methacrylic acid ester copolymers with acid ionizable groups ("EUDRAGIT™"), such as "EUDRAGIT™ L 30D", "EUDRAGIT™ RL 30D", "EUDRAGIT™ RS 30D", "EUDRAGIT™ L 100-55", and "EUDRAGIT™ L 30D-55".

Application of the enteric coating to composition can be accomplished by any method known in the art for applying enteric coatings. For example, but not by way of limitation, the enteric polymers can be applied using organic solvent based solutions containing from 5 to 10% w/w polymer for spray applications and up to 30% w/w polymer for pan coatings. Solvents that are commonly in use include, but are not limited to, acetone, acetone/ethyl acetate mixtures, methylene chloride/methanol mixtures, and tertiary mixtures containing these solvents. Some enteric polymers, such as methacrylic acid-methacrylic acid ester copolymers can be applied using water as a dispersant.

Furthermore, plasticizers can be added to the enteric coating to prevent cracking of the coating film. Suitable plasticizers include the low molecular weight phthalate esters, such as diethyl phthalate, acetylated monoglycerides, triethyl citrate, polyethyl glycoltributyl citrate and triacetin. Generally, plasticizers are added at a concentration of 10% by weight of enteric coating polymer weight. Other additives such as emulsifiers, for example detergents and simethicone, and powders, for example talc, may be added to the coating to improve the strength and smoothness of the coating. Additionally, pigments may be added to the coating to add color to the pharmaceutical formulation.

In certain embodiments, the composition comprising an extract or one or more compounds in an extract disclosed herein is formulated with a compound or compounds which neutralize stomach acid. Alternatively, the pharmaceutical composition containing an extract or one or more compounds in an extract disclosed herein is administered either concurrent with or subsequent to administration of a pharmaceutical composition which neutralize stomach acid. Compounds, such as antacids, which are useful for neutralizing stomach acid include, but are not limited to, aluminum carbonate, aluminum hydroxide, bismuth subnitrate, bismuth subsalicylate, calcium carbonate, dihydroxyaluminum sodium carbonate, magaldrate, magnesium carbonate, magnesium hydroxide, magnesium oxide, and mixtures thereof.

In certain embodiments, composition comprising an extract or one or more compounds in an extract disclosed herein is administered with a substance that inactivates or inhibits the action of stomach enzymes, such as pepsin. Alternatively, the pharmaceutical composition containing the proanthocyanidin polymer composition is administered either concurrent with or subsequent to administration of a pharmaceutical composition active to inactivate or inhibit the action of stomach enzymes. For example, but not by way of limitation, protease inhibitors, such as aprotin, can be used to inactivate stomach enzymes.

In certain embodiments, the composition comprising an extract or one or more compounds in an extract disclosed herein is formulated with a compound or compounds which inhibit the secretion of stomach acid. Alternatively, the pharmaceutical composition is administered either concurrent with or subsequent to administration of a pharmaceutical composition active to inhibit the secretion of stomach acid. Compounds which are useful for inhibiting the secretion of stomach acid include, but are not limited to, ranitidine, nizatidine, famotidine, cimetidine, and misoprostol.

Cosmetic Formulations and Personal Care Products

In certain embodiments, the disclosure relates to a cosmetic formulation comprising an extract or one or more compounds in an extract disclosed herein and cosmetically acceptable excipient or additive. In certain embodiments, the disclosure relates to a solid or liquid soap or lotion comprising an extract or one or more compounds in an extract disclosed herein and a fatty acid.

In certain embodiments, additives can be selected from the group consisting of oily bodies, surfactants, emulsifiers, fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, film formers, antidandruff agents, swelling agents, insect repellents, hydrotropes, solubilizers, preservatives, perfume oils and dyes.

In certain embodiments, additives are selected from the group consisting of surfactants, emulsifiers, fats, waxes, stabilizers, deodorants, antiperspirants, antidandruff agents and perfume oils.

As used herein, cosmetic preparations can mean care agents. Care agents are understood as meaning care agents for skin and hair. These care agents include, inter alia, cleansing and restorative action for skin and hair.

In certain embodiments, preparations may be cosmetic and/or dermopharmaceutical preparations, e. g. hair shampoos, hair lotions, foam baths, shower baths, creams, gels, lotions, alcoholic and aqueous/alcoholic solutions, emulsions, wax/fat compositions, stick preparations, powders or ointments.

Surfactants (or Surface-active substances) that may be present are anionic, non-ionic, cationic and/or amphoteric surfactants, the content of which in the compositions is usually about 1 to 70% by weight, preferably 5 to 50% by weight and in particular 10 to 30% by weight. Typical examples of anionic surfactants are soaps, alkylbenzenesulfonates, alkanesulfonates, olefin sulfonates, alkyl ether sulfonates, glycerol ether sulfonates, α-methyl ester sulfonates, sulfo fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, e.g. acyl lactylates, acyl tartrates, acyl glutamates and acyl aspartates, alkyl oligoglucoside sulphates, protein fatty acid condensates (in particular wheat-based vegetable products) and alkyl (ether) phosphates. If the anionic surfactants contain polyglycol ether chains, these may have a conventional homologous distribution, but preferably have a narrowed homologous distribution. Typical examples of non-ionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. If the non-ionic surfactants contain polyglycol ether chains, these may have a conventional homologous distribution, but preferably have a narrowed homologous distribution. Typical examples of cationic surfactants are quaternary ammonium compounds, e.g. dimethyldistearyl-ammonium chloride, and ester quats, in particular quaternized fatty acid trialkanolamine ester salts. Typical examples of amphoteric or zwitterionic surfactants are alkylbetaines, alkylamidobetaines, aminopropionates, aminoglycinates, imidazolinium-betaines and sulfobetaines. Said surfactants are known compounds. With regard to structure and preparation of these substances, reference may be made to relevant review works.

Typical examples of particularly suitable mild, i.e. particularly skin-compatible surfactants are fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylamidobetaines, amphoacetals and/or protein fatty acid condensates, the latter preferably based on wheat proteins.

Suitable oily bodies are, for example, alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, for example myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxycarboxylic acids with linear or branched $C_6$-$C_{22}$-fatty alcohols, in particular dioctyl malates, esters of linear and/or branched fatty acids with polyhydric alcohols (for example propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, for example dicaprylyl carbonates (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, for example dicaprylyl ether (Cetiol® OE), ring-opening products of epoxidized fatty acid esters with polyols, silicone oils (cyclomethicones, silicon methicone types, inter alia) and/or aliphatic or naphthenic hydrocarbons, for example squalane, squalene or dialkylcyclohexanes.

Suitable emulsifiers are, for example, nonionogenic surfactants from at least one of the following groups:

addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical;

alkyl and/or alkenyl oligoglycosides having 8 to 22 carbon atoms in the alk(en)yl radical and the ethoxylated analogs thereof;

addition products of from 1 to 15 mol of ethylene oxide onto castor oil and/or hydrogenated castor oil;

addition products of from 15 to 60 mol of ethylene oxide onto castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;

partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;

mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

block copolymers, e.g. polyethylene glycol-30 dipolyhydroxystearates;

polymer emulsifiers, e.g. Pemulen® grades (TR-1, TR-2) from Goodrich;

polyalkylene glycols and glycerol carbonate.

The addition products of ethylene oxide and/or of propylene oxide onto fatty alcohols, fatty acids, alkylphenols or onto castor oil are known, commercially available products. These are homologous mixtures whose average degree of alkoxylation corresponds to the ratio of the amounts of ethylene oxide and/or propylene oxide and substrate with which the addition reaction is carried out. C12/18-fatty acid mono- and diesters of addition products of ethylene oxide onto glycerol are known as refatting agents for cosmetic preparations.

Alkyl and/or alkenyl oligoglycosides can be prepared by reacting glucose or oligosaccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value that is based on a homologous distribution customary for such technical-grade products.

Typical examples of suitable partial glycerides are hydroxy stearic acid monoglyceride, hydroxy stearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linoleic acid monoglyceride, linoleic acid diglyceride, erucic acid monoglyceride, erucic acid diglyceride, tartaric acid monoglyceride, tartaric acid diglyceride, citric acid monoglyceride, citric acid diglyceride, malic acid mono-glyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide onto said partial glycerides.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of 1 to 30 mol, preferably 5 to 10 mol, of ethylene oxide onto said sorbitan esters.

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Furthermore, zwitterionic surfactants can be used as emulsifiers. The term "zwitterionic surfactants" refers to those surface-active compounds that carry at least one quaternary ammonium group and at least one carboxylate and one sulfonate group in the molecule. Particularly suitable zwitterionic surfactants are the betaines, such as N-alkyl-N,N-dimethylammonium glycinates, for example cocoalkyldimethylammonium glycinate, N-acylaminopropyl-N,N-dimethylammonium glycinates, for example cocoacyl-amino-propyldimethylammonium glycinate, and 2-alkyl-3-carboxymethyl-3-hydroxyethylimidazolines having in each case 8 to 18 carbon atoms in the alkyl or acyl group, and cocoacylamino-ethylhydroxyethyl-carboxymethyl glycinate. Particular preference is given to the fatty acid amide derivative known under the CTFA name Cocamidopropyl Betaine. Likewise suitable emulsifiers are ampholytic surfactants. The term "ampholytic surfactants" means those surface-active compounds that, apart from a $C_{8/18}$-alkyl or -acyl group in the molecule, contain at least one free amino group and at least one —$CO_2H$ or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyl-taurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkyl aminopropionate, cocoacyl-aminoethyl aminopropionate and $C_{12/18}$-acylsarcosine. Finally, cationic surfactants are also suitable emulsifiers, those of the ester quat type, preferably methylquaternized difatty acid triethanolamine ester salts, being particularly preferred.

Fats and waxes that can be used are described in the following text. Typical examples of fats are glycerides, i.e. solid or liquid vegetable or animal products which consist essentially of mixed glycerol esters of higher fatty acids, suitable waxes are inter alia natural waxes, for example candelilla wax, carnauba wax, japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), for example montan ester waxes, sasol waxes, hydrogenated jojoba waxes, and synthetic waxes, for example polyalkylene waxes and polyethylene glycol waxes. In addition to the fats, suitable additives are also fat-like substances, such as lecithins and phospholipids.

The term "lecithins" is understood by the person skilled in the art as meaning those glycerophospholipids which form from fatty acids, glycerol, phosphoric acid and choline by esterification. Lecithins are thus frequently also known as phosphatidylcholines (PC). Examples of natural lecithins which may be mentioned are the cephalins, which are also referred to as phosphatidic acids and represent derivatives of 1,2-diacyl-sn-glycerol-3-phosphoric acids. By contrast, phospholipids are usually understood as meaning mono- and, preferably, diesters of phosphoric acid with glycerol (glycerophosphates), which are generally considered to be fats. In addition, sphingosines and sphingolipids are also suitable.

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, for example fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Bodying agents and thickeners that can be used are described in the following text. Suitable bodying agents are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, aerosil grades (hydrophilic silicas), polysaccharides, in particular xanthan gum, guar guar, agar agar, alginates and Tyloses, carboxymethylcellulose and hydroxyethylcellulose, and also relatively high molecular weight polyethylene glycol mono- and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone, surfactants, for example ethoxylated fatty acid glycerides, esters of fatty acids with polyols for example pentaerythritol or trimethylolpropane, fatty alcohol ethoxylates having a narrowed homolog distribution or alkyl oligoglucosides, and electrolytes such as sodium chloride and ammonium chloride.

Superfatting agents which can be used are for example lanolin and lecithin, and polyethoxylated or acylated lanolin and lecithin derivatives, polyol fatty acid esters, monoglycerides and fatty acid alkanolamides, the latter also serving as foam stabilizers.

Stabilizers which can be used are metal salts of fatty acids, for example magnesium, aluminium and/or zinc stearate or ricinoleate.

Polymers that can be used are described in the following text. Suitable cationic polymers are, for example, cationic cellulose derivatives, for example a quaternized hydroxyethylcellulose obtainable under the name Polymer JR 400® from Amerchol, cationic starch, copolymers of diallylammonium salts and acryl amides, quaternized vinylpyrrolidone-vinylimidazole polymers, for example Luviquat® (BASF), condensation products of polyglycols and amines, quaternized collagen polypeptides, for example lauryldimonium hydroxypropyl hydrolysed collagen (Lamequat® L/Grunau), quaternized wheat polypeptides, polyethyleneimine, cationic silicone polymers, for example amodimethicones, copolymers of adipic acid and dimethylaminohydroxypropyldiethylenetriamine (Cartaretins®/Sandoz), copolymers of acrylic acid with dimethyl diallylammonium chloride (Merquat® 550/Chemviron), polyaminopolyamides and cross linked water-soluble polymers thereof, cationic chitin derivatives, for example quaternized chitosan, optionally in microcrystalline dispersion, condensation products from dihaloalkyls, for example dibromobutane with bisdialkylamines, for example bis-dimethylamino-1,3-propane, cationic guar gum, for example Jaguar® CBS, Jaguar® C-17, Jaguar® C-16 from Celanese, quaternized ammonium salt polymers, for example Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamidopropyltrimethylammonium chloride-acrylate copolymers, octylacrylamide-methyl methacrylate-tert-butylamino-ethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones.

Suitable silicone compounds are, for example, dimethylpolysiloxanes, methylphenylpolysiloxanes, cyclic silicones, and amino-, fatty-acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethylsiloxane units and hydrogenated silicates.

Deodorants and antimicrobial agents that can be used are described in the following text. Cosmetic deodorants counteract, mask or remove body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents. Suitable antimicrobial agents are, in principle, all substances effective against gram-positive bacteria, for example 4-hydroxybenzoic acid and its salts and esters, N-(4-chlorophenyl)-N'-(3,4-dichloro-phenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methyl-ethyl)phenol, 2-benzyl-4-chlorophenol, 3-(4-chlorophenoxy)-1,2-propanediol, 3-iodo-2-propynyl butylcarbamate, chlorohexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, for example n-octylsalicylamide or n-decylsalicylamide.

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing the formation of odor. Other substances which are suitable esterase inhibitors are sterol sulfates or phosphates, for example lanosterol, cholesterol, campesterol, stigmasterol and sitosterol sulfate or phosphate, dicarboxylic acids and esters thereof, for example glutaric acid, monoethyl glutarate, diethyl glutarate, adipic acid, monoethyl adipate, diethyl adipate, malonic acid and diethyl malonate, hydroxycarboxylic acids and esters thereof, for example citric acid, malic acid, tartaric acid or diethyl tartrate, and zinc glycinate.

Suitable odor absorbers are substances which are able to absorb and largely retain odor-forming compounds. They lower the partial pressure of the individual components, thus also reducing their rate of diffusion. It is important that in this process perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives", for example extracts of labdanum or styrax or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, for example civet and castoreum. Typical synthetic fragrance compounds are products of the ester, ether, aldehyde, ketone, alcohol and hydro-carbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, oil of cloves, melissa oil, mint oil, cinnamon leaf oil, linden flower oil, juniper berry oil, vetiver oil, olibanum oil, galbanum oil, labdanum oil and lavandin oil. Preference is given to using bergamot oil, dihydromyrcenol, lilial, lyral, citronellol, phenyl ethyl alcohol, α-hexyl cinnamal dehy de, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evemyl, iraldein gamma, phenylacetic acid, geranyl acetate, benzyl acetate, rose oxide, romilat, irotyl and floramat alone or in mixtures.

Antiperspirants reduce the formation of perspiration by influencing the activity of the eccrine sweat glands, thus counteracting underarm wetness and body odor. Aqueous or anhydrous formulations of antiperspirants typically comprise one or more of the following ingredients: astringent active ingredients, oil components, nonionic emulsifiers, coemulsifiers, bodying agents, auxiliaries, for example thickeners or complexing agents, and/or nonaqueous solvents, for example ethanol, propylene glycol and/or glycerol.

Suitable astringent antiperspirant active ingredients are primarily salts of aluminum, zirconium or of zinc. Such suitable antihydrotic active ingredients are, for example, aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, e.g. with amino acids, such as glycine. In addition, customary oil-soluble and water-soluble auxiliaries may be present in antiperspirants in relatively small amounts. Such oil-soluble auxiliaries may, for example, be anti-inflammatory, skin-protective or perfumed ethereal oils, synthetic skin-protective active ingredients and/or oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, for example xanthan gum, hydroxyethylcellulose, polyvinylpyrrolidone or high molecular weight polyethylene oxides.

Film formers that can be used are described in the following text. Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

Suitable antidandruff active ingredients are piroctone olamine (1-hydroxy-4-methyl-6-(2,4,4-trimethylpentyl)-2-(1H)-pyridinone monoethanolamine salt), Baypival® (climbazole), Ketoconazole®, (4-acetyl-1-{-4-[2-(2,4-dichlorophenyl) r-2-(1H-imidazol-1-ylmethyl]-1,3-dioxylan-c-4-ylmethoxyphenyl}piperazine, ketoconazole, elubiol, selenium disulfide, colloidal sulfur, sulfur polyethylene glycol sorbitan monooleate, sulfur ricinol polyethoxylate, sulfur tar distillates, salicyclic acid (or in combination with hexachlorophene), undecylenic acid monoethanolamide sulfosuccinate Na salt, Lamepon® UD (protein undecylenic acid condensate), zinc pyrithione, aluminum pyrithione and magnesium pyrithione/dipyrithione magnesium sulfate.

The swelling agents for aqueous phases may be montmorillonites, clay mineral substances, Pemulen, and alkyl-modified Carbopol grades (Goodrich).

Suitable insect repellents are N,N-diethyl-m-toluamide, 1,2-pentanediol or ethyl butylacetylaminopropionate.

To improve the flow behavior, hydrotropes, for example ethanol, isopropyl alcohol, or polyols, can be used. Polyols which are suitable here preferably have 2 to 15 carbon atoms and at least two hydroxyl groups. The polyols can also contain further functional groups, in particular amino groups, or be modified with nitrogen. Typical examples are:

glycerol;

alkylene glycols, for example, ethylene glycol, diethylene glycol, propylene glycol, butylene glycol, hexylene glycol, and polyethylene glycols with an average molecular weight of from 100 to 1 000 daltons;

technical-grade oligoglycerol mixtures with a degree of self-condensation of from 1.5 to 10, for example, technical-grade diglycerol mixtures with a diglycerol content of from 40 to 50% by weight;

methylol compounds, such as trimethylolethane, trimethylolpropane, trimethylol-butane, pentaerythritol and dipentaerythritol;

lower alkyl glucosides, in particular those with 1 to 8 carbon atoms in the alkyl radical, for example methyl and butyl glucoside;

sugar alcohols with 5 to 12 carbon atoms, for example sorbitol or mannitol, sugars with 5 to 12 carbon atoms, for example glucose or sucrose;

amino sugars, for example glucamine;

dialcohol amines, such as diethanolamine or 2-amino-1, 3-propanediol.

Suitable preservatives are, for example, phenoxyethanol, formaldehyde solution, parabenes, pentanediol or sorbic acid, and the other classes of substance listed in Annex 6, Part A and B of the Cosmetics Directive.

Perfume oils which may be used are preferably mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamom, costus, iris, calmus), woods (pine wood, sandalwood, guaiac wood, cedarwood, rosewood), herbs and grasses (tarragon, lemon grass, sage, thyme), needles and branches (spruce, fir, pine, dwarf-pine), resins and balsams (galbanum, elemi, benzoin, myrrh, olibanum, opoponax). Also suitable are animal raw materials, for example civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include predominantly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evemyl, iraldein gamma, phenylacetic acid, geranyl acetate, benzyl acetate, rose oxide, romilat, irotyl and floramat alone or in mixtures.

Medical Device Coatings, Wound Dressings, and Irrigation

In certain embodiments, the disclosure relates to a medical device comprising a coating comprising an extract or one or more compounds in an extract disclosed herein optionally in combination with another antibiotic. In certain embodiments, the medical device is an ear tube, eye lenses, contact lenses, coronary stent, metal screw, pin, plate, rod, catheter, artificial knee, cardioverter defibrillator, artificial hip, heart pacemaker, breast implant, spine screws, rods, and discs, intra-uterine devices In certain embodiments, the disclosure relates to a wound dressing comprising an extract or one or more compounds in an extract disclosed herein wherein the wound dress comprises an absorbent pad and optionally an adhesive optionally in combination with another antibiotic agent. In certain embodiments, the wound dressing is a foam or compression dressing or a cover dressing such as wraps, gauze and tape.

In certain embodiments, the wound dressing comprises alginate or collagen.

In certain embodiments, the wound dressing a hydrocolloid dressing, e.g., carboxy-methylcellulose and gelatin optionally in a polyurethane foam or film, optionally comprising one or more agents selected from, pectin, polysaccharides, and an adhesive.

In certain embodiments, the wound dressing is a hydrogel. Hydrogels are polymers that contain a high content, e.g., greater than 40, 50, 60, 70, 80, 90, or 95%, of hydroxy and/or carboxyl containing monomers or salts thereof, e.g., vinyl alcohol, acrylic acid, 2-hydroxyethylmethacrylate monomers, which can be co-polymers to provide varying degrees of hydration, e.g., copolymerization with ethylene glycol dimethacrylate. Due to the hydrophilic monomers, the hydrogels typically absorb water to contain greater than 70, 80, 85, 90, 95% water by weight. Contemplated hydrogel dressings include: amorphous hydrogel, which are a free-flowing gel that are typically distributed in tubes, foil packets and spray bottles; an impregnated hydrogel, which are typically saturated onto a gauze pad, nonwoven sponge ropes and/or strips; or a sheet hydrogel which are gel held together by a fiber mesh.

A flow of wound rinse/irrigation solution is applied across an open wound surface to achieve wound hydration, to remove deeper debris, and to assist with the visual examination. In certain embodiments, the disclosure relates to methods of irrigating using a solution comprising an extract or one or more compound in an extract disclosed herein. In certain embodiments, the disclosure relates to a wound rinse comprising an extract or one or more compounds in an extract disclosed herein optionally in combination with normal saline, sterile water, detergent, surfactant, preservatives, or iodine.

In certain embodiments, the disclosure contemplate a kit comprising a container comprising an extract or one or more compounds in an extract discloses herein optionally comprising a second container comprising a solution, normal saline, sterile water, detergent, surfactant, preservatives, iodine, hydrogen peroxide, or sodium hypochlorite.

EXAMPLES

Collection and Crude Extraction of Plant Materials

Fresh leaves of the European Chestnut (Castanea sativa Mill., Fagaceae) were collected from wild populations in the months of May-July (2012-2014) in the Rionero-Alto Bradano region of the Basilicata Province in southern Italy following standard guidelines for collection of wild specimens. Collections were made on private land with the permission of the landowner. Voucher specimens (CQ-309) were deposited at the Herbarium Lucanum (HLUC) at the University della Basilicata in Potenza, Italy and the Emory University Herbarium (GEO) in Atlanta, Ga., USA. The specimens were identified using the standard Italian Flora and identification was confirmed at HLUC. Chestnut leaves were shade-dried, ground with a blender, and vacuum sealed with silica packets prior to shipment to the US (under USDA permit) for extraction and analysis. Upon arrival at the lab, leaves were further ground into a fine powder with a Thomas Wiley Mill at a 2 mm mesh size (Thomas Scientific).

Extraction and Purification of QSI-containing Fractions

Crude methanol extracts (Extract 224) of the ground leaves were created by maceration of the plant materials at room temperature using a ratio of 1 g dry leaves: 10 mL MeOH for two successive periods of 72 hours, with daily agitation. Filtered extracts were combined, concentrated at reduced pressure and a temperature<40° C. with rotary evaporators, and lyophilized before being re-suspended in water and partitioned in succession with hexane, ethyl acetate and butanol. The resulting non-aqueous partitions were dried over anhydrous $Na_2SO_4$, concentrated in vacuo, and lyophilized before testing for activity.

The most active partition (ethyl acetate, extract 224C) was subjected to further fractionation using a CombiFlash® Rf+ (Teledyne ISCO) flash chromatography system using a RediSep Rf Gold silica column. Extract 224C was bonded to Celite 545 (Acros Organics) at a 1:4 ratio and dry-loaded using a RediSep dry load cartridge. The mobile phase consisted of (A) hexane, (B) EtOAc, and (C) MeOH. The linear gradient begins with 100% A for 6.3 column volumes (CV), then 50:50 A:B at 25.3 CV, to 100% B at 63.3 CV, which is held till 69.6 CV, then to 70:30 B:C at 88.6 CV which is held till 94.9 CV. The chromatography was monitored at 254 and 280 nm, as well as via ELSD. The resulting fractions were combined into 5 fractions. Following further bioassay testing, it was determined that the fraction which eluted from 30-40 CV (224C-F2) was most active. The full extract fractionation scheme is presented in FIG. 2.

Characterization by HPLC and LC-FTMS

An analytical HPLC-method was developed for the purposes of characterization of 224 and fractions. The analysis was performed on an Agilent 1260 Infinity system running OpenLab CDS ChemStation (Agilent Technologies, Santa Clara, Calif., USA) with an Agilent ZORBAX Eclipse XDB-$C_{18}$ (250 mm×4.6 mm, 5 µm) column with compatible guard column at a column temperature of 40° C. Mobile phase reagents were HPLC-grade and purchased from Fisher Scientific, except for the Type 1 water, which was obtained from an EMD Millipore MILLI-Q water system (Billerica, Mass.). Mobile phase consisted of a linear gradient elution 0.1% formic acid in acetonitrile (A) and 0.1% formic acid in water (B) at a flow rate of 1 mL/min. Initial conditions were 98:2 (A:B) changing to 70:30 (A:B) at 50 min, to 2:98 (A:B) at 70 min and held until 85 min., Samples were prepared in DMSO and 10 µL injections were made. Chromatograms were monitored at 254 nm and 314 nm.

Liquid chromatography-Fourier transform mass spectrometry (LC-FTMS) was performed on 224C-F2 using a Shimadzu SIL-ACHT and Dionex 3600SD HPLC pump with a modification of the previous chromatographic conditions. A 20 µL injection at ambient temperature with 0.1% formic acid in Optima LC/MS acetonitrile (Fisher Scientific) (A) and 0.1% formic acid in water (B) at a flow rate of 1 mL/min. Initial conditions were 98:2 (A:B) changing to 64:36 (A:B) at 12 min, to 52:48 (A:B) at 86 min, 2:98 (A:B) at 102.6 min and held until 117.6 min before returning to initial conditions to equilibrate the column. The data was acquired in $MS^1$ mode scanning from a m/z of 150-1500 on a Thermo Scientific LTQ-FT Ultra MS in negative ESI mode and processed with Thermo Scientific Xcalibur 2.2 SP1.48 software (San Jose, Calif.). The capillary temperature was 275.0° C., sheath gas of 60, source voltage and current 5.0 kV and 100.0 µA, and the capillary voltage −49.0 V.

Putative compounds were determined for compounds present in the bioactive active region of 224C-F2' s chromatogram (retention time of 21-49 min). The Dictionary of Natural Products (CRC Press) and Scifinder (Chemical Abstracts Service) were searched in May 2015 using similar methodology. The high resolution mass of the compound was determined from the LC-FTMS data and the database searched for all compounds within ±0.5 Da. The resulting compounds were limited to only those identified in the genus Castanea, for DNP several entries for the misspelling "Castaneae" were also included. The molecular formulas of the remaining compounds were compared to empirical formulas derived from the MS data and those that matched the experimental molecular mass with a delta of less than 100 ppm were evaluated further. Only small molecules were considered for further evaluation. Publications on the remaining small molecules were reviewed and the presence of the compound in the genus was verified.

In addition to examining LC-FTMS data and fragmentation patterns as described above, a number of natural products were specifically searched for in 224C-F2: chlorogenic acid, ellagic acid hyperoside, isoquercitrin and rutin. Standards of chlorogenic acid and ellagic acid (MP Biomedicals, Solon Ohio) and hyperoside (Chromadex, Irvine, Calif.) were run on the analytical HPLC method described above to determine retention times. The others were examined by MS fragmentation patterns and published UV-Vis spectra. Standards were evaluated for purity via HPLC-DAD.

Bacterial Strains, Plasmids, and Culture Media.

S. aureus cultures were grown in Tryptic Soy Broth (TSB) or Tryptic Soy Agar (TSA). Cation-adjusted Mueller-Hinton broth (CAMHB) was used for minimum inhibitory concentration (MIC) testing of S. aureus. The bacterial strains and plasmids used in this study are described in Table 1.

TABLE 1

Description of bacterial strains and plasmids used.

| Designation | Species | Other Characteristics* |
|---|---|---|
| AH408; SA502A | Staphylococcus aureus | agr group II |
| AH430 | Staphylococcus aureus | SA502a + pDB59 cmR, yfp reporter, agr group II |
| AH845 | Staphylococcus aureus | agr group I |
| AH1263; LAC | Staphylococcus aureus | CA-MRSA, PFT USA300, agr group I |
| AH1677 | Staphylococcus aureus | AH845 + pDB59 cmR, yfp reporter, agr group I |
| AH1747 | Staphylococcus aureus | MW2 + pDB59 cmR, yfp reporter, agr group III |
| AH1872 | Staphylococcus aureus | MN EV(407) + pDB59 cmR, yfp reporter, agr group IV |
| AH2759 | Staphylococcus aureus | AH1263 agr P3:lux |
| AH3052 | Staphylococcus aureus | AH1263 Δspa |
| F0392; HM-262 | Streptococcus mitis | HMP, oral cavity isolate |
| FS1; NR-13441 | Corynebacterium striatum | Clinical isolate from Italy, 2005-2007 |
| MGAS15252; NR-33709 | Streptococcus pyogenes | serotype M59, Group A Streptococcus (GAS) |
| HL005PA2; HM-493 | Propionibacterium acnes | HMP, skin isolate |
| MN EV(407) | Staphylococcus aureus | agr group IV |
| MW-2 | Staphylococcus aureus | agr group III |
| NIHLM001; HM-896 | Staphylococcus epidermidis | HMP, 2008 skin isolate from alar crease from healthy volunteer |
| NRS-116; NR-45922 | Staphylococcus haemolyticus | Glycopeptide intermediate, 2002 surgical isolate |
| NR5385; NR-46071 | Staphylococcus aureus | HA-MRSA, PFT USA500, MLST ST8, SCC mecIV, agr group I, sea+, seb+ |
| SK46; HM-109 | Corynebacterium amycolatum | HMP, skin isolate on arm of healthy volunteer |
| SK58; HM-114 | Micrococcus luteus | HMP, skin isolate on arm of healthy volunteer |
| SK66; HM-120 | Staphylococcus warneri | HMP, skin isolate on arm of healthy volunteer |
| UAMS-1 | Staphylococcus aureus | MSSA, osteomyelitis isolate |
| UAMS-929 | Staphylococcus aureus | isogenic sarA mutant of UAMS-1 |

*Escherichia coli* cultures were grown in Luria-Bertani (LB) broth or on LB agar plates supplemented with 100 μg mL$^{-1}$ ampicillin (Amp) as required for plasmid maintenance. *S. aureus* chromosomal markers or plasmids were selected for with 10 μg mL$^{-1}$ of chloramphenicol (Cam) or erythromycin (Erm). *Staphylococcus warneri* cultures were grown in TSB or Brain-Heart Infusion (BHI) agar. *Micrococcus luteus* cultures were grown in nutrient broth or agar. *Streptococcus mitis, Streptococcus pyogenes, Corynebacterium amycolatum, Staphylococcus haemolyticus* and *Staphylococcus epidermidis* cultures were grown in BHI broth or TSA with 5% sheep blood. *Corynebacterium striatum* cultures were grown in TSB or TSA with 5% sheep blood. *Propionibacterium acnes* cultures were grown in Reinforced Clostridial Medium (RCM) broth or TSA with 5% sheep blood under static, anaerobic conditions generated by GasPak EZ Systems. Unless otherwise stated, all broth cultures were grown at 37° C. with shaking at 250 rpm.

Minimum Inhibitory Concentration (MIC)

Extract 224 and fractions were examined for minimum inhibitory concentrations (MIC) against strains representing the four agr alleles (AH430, AH1677, AH1747, AH1872), biofilm test strain (UAMS-1) and a USA500 strain (NRS385), which was used in δ-toxin quantification experiments. Clinical Laboratory Standards Institute (CL SI) M100-S23 guidelines for microtiter broth dilution testing were followed. Controls include the vehicle, and antibiotics: Kanamycin (Kan) and Amp (MP Biomedicals Inc). All concentrations were tested in triplicate and repeated twice on different days. Briefly, overnight cultures in CAMHB were standardized by OD to 5×10$^5$ CFU/mL, and this was confirmed by plate counts. Two-fold serial dilutions were performed on a 96-well plate (Falcon 35-1172) to achieve a test range of 512-0.25 μg mL$^{-1}$ for extracts and 64-0.03125 μg mL$^{-1}$ for Amp and Kan. Plates were incubated at 37° C. for 18 hrs. under static conditions. Plates were read at an OD 600 nm in a Cytation 3 multimode plate reader (Biotek) at 0 and 18 hrs. post inoculation. The following formula, which takes into account the impact of extract color and vehicle on the OD, was used as described in Quave et al., J Ethnopharmacol. 2008, 118(3):418-28:

$$\% \text{ Inhibition} = \left[1 - \left(\frac{OD_{t18} - OD_{t0}}{OD_{vc18} - OD_{vc0}}\right)\right] \times 100$$

with $OD_{t18}$=OD of the test well at 18 hrs., $OD_{t0}$=OD of the test well at 0 hrs., $OD_{vc18}$=OD of the vehicle control well at 18 hrs, and $OD_{vc0}$=OD of the vehicle control well at 0 hrs. MIC$_{50}$ and MIC$_{90}$ values were assigned based on the concentration at which at least 50 or 90% inhibition of growth was observed as determined by OD, respectively.

Growth inhibition of the refined extract, 224C-F2, was also assessed for impact on the normal skin microflora. In all cases, with the exception of *P. acnes*, the appropriate CLSI method for MIC determination by broth microdilution was employed. Briefly, MICs for *Staphylococcus warneri, S. epidermidis, S. haemolyticus* and *Micrococcus luteus* were determined using the above described M100-S23 CLSI method for *S. aureus* with vehicle and antibiotic controls. Amp and Kan (MP Biomedicals Inc) were used in all *staphylococcal* tests; Amp, Erm (Sigma Aldrich) and clindamycin, Clin (MP Biomedicals) were used for *M. luteus* controls. MICs for *Streptococcus pyogenes* and *S. mitis* were determined using the M100-S23 CLSI method in CAMHB with 3% lysed horse blood (LHB), incubated at 37° C. for 24 hrs under static conditions, with Amp and Erm as antibiotic controls. MICs for *Corynebacterium striatum* and *C. amycolatum* followed the M45-A2 CLSI method in CAMHB with 3% LHB, incubated at 35° C. for 24 hrs under static conditions, with Amp and Erm as antibiotic controls. MICs for *Propionibacterium acnes* were based on a previous method using BHI supplemented with 1% dextrose, incubated at 37° C. for 72 hrs under static, anaerobic conditions.

Quorum Quenching Assays with Reporter Strains

Extracts were tested for quorum quenching activity against all four agr types using agr P3-YFP reporter strains AH1677 (type I), AH430 (type II), AH1747 (type III), and AH1872 (type IV), as well as agr P3-lux (type I) reporter strain AH2759. Overnight cultures of reporter strains that were grown in TSB supplemented with Cam were inoculated at a dilution of 1:250 into fresh TSB containing Cam. 100 µL aliquots were added to 96-well microtiter plates (Costar 3603) containing 100 µL aliquots of TSB containing Cam and 2-fold serial dilutions (0.1-200 µg mL$^{-1}$) of extracts 224, 224C, and 224C-F2. After mixing, the effective inoculum dilution was 1:500 and the final extract concentrations ranged from 0.05-100 µg mL$^{-1}$, with a final DMSO concentration of 1% (v/v) in all wells. Four dilution series were prepared for each reporter/extract combination, and in addition 4 mock vehicle (DMSO) dilution series were included for each reporter strain. Microtiter plates were incubated at 37° C. with shaking (1000 rpm) in a Stuart SI505 incubator (Bibby Scientific, Burlington, N.J.) with a humidified chamber. Fluorescence (top reading, 493 nm excitation, 535 nm emission, gain 60) and optical density (OD) readings at 600 nm, or luminescence and OD$_{600}$ readings in the case of reporter AH2759, were recorded at 30 min increments using a Tecan Systems (San Jose, Calif.) Infinite M200 plate reader.

Hemolytic Activity by Red Blood Cell Lysis Assay

The quorum quenching activity of extracts was assessed by measuring the hemolytic activity of culture supernatants on rabbit red blood cell lysis. Overnight cultures of an Erm sensitive variant of USA300 strain LAC, AH1263 and an hla::Tn551 (AH1589) mutant of AH1263 were inoculated 1:500 into 5 ml of TSB (in 17×150 mm culture tubes) containing extracts 224, 224C, or 224CF2 at concentrations of 6.25, 12.5, 25, 50 and 100 µg mL$^{-1}$. In all tubes containing extract the mock vehicle (DMSO) concentration was held constant at 1% (v/v). Vehicle control tubes containing 1% DMSO were similarly prepared for AH1263, AH1589 well as for an Δagr::tetM (AH1292) mutant of AH1263. All tubes were incubated at 37° C. with shaking (250 rpm), and growth was monitored by periodically transferring 100 µL of culture to a 96-well microtiter plate and reading OD$_{600}$ in a Tecan Systems (San Jose, Calif.) Infinite M200 plate reader. Following 6 hrs of incubation, 600 µL of each culture was filter sterilized using cellulose acetate SpinX 0.22 µm filters (Corning).

To quantify hemolytic activity, the filter sterilized culture supernatants were serially diluted in 2-fold steps (from 0.04-100%) in TSB, and 50 µL aliquots were dispensed in quadruplicate into 96-well microtiter plates. Rabbit erythrocytes, prepared from defibrinated blood (Hemostat Laboratories, Dixon, Calif.) by washing 3 times with 1.1×PBS and resuspending in 1.1× PBS at 1% (v/v), were added to the microtiter plates at 50 µL per well (yielding a final erythrocyte concentration of 0.5% (v/v)). The erythrocytes and culture supernatants were mixed thoroughly and incubated statically at room temperature for 2 hrs. Hemolysis was detected by the loss of turbidity as measured at OD$_{630}$ using a Tecan Systems (San Jose, Calif.) Infinite M200 plate reader. Relative hemolytic activities were obtained by using KaleidaGraph 4.1.3 (Synergy Software, Reading, Pa., USA) to perform 4-parameter logistic fits of the turbidity data in order to determine the concentration of supernatant that resulted in 50% red blood cell lysis.

Western Blot for Alpha-Hemolysin

An overnight culture of *S. aureus* AH3052 Δspa was inoculated into 5 mL of TSB at 1:500 and grown at 37° C. with shaking (250 rpm), in the presence of either DMSO or one of the extracts (224, 224C or 224C-F2) at concentrations of 6.25, 12.5, 25, 50 and 100 µg mL$^{-1}$. Following 8 hours of incubation, 600 µL of each culture was filter sterilized using a cellulose acetate SpinX 0.22 µm filter (Corning) and the filter sterilized media was stored at −20° C. The filtered media was electrophoresed on 13% SDS-PAGE gels and transferred to nitrocellulose membranes (Bio-Rad). Membranes were blocked overnight at 4° C. in TBST (20 mM Tris [pH 7.5], 150 mM NaCl, 0.1% Tween 20) with 5% nonfat dry milk then washed 3 times with TB ST. Hla was detected using a polyclonal rabbit anti-Hla antibody (Shlievert Lab, University of Iowa) at a 1:5000 dilution and a goat anti-rabbit HRP secondary antibody (Jackson ImmunoResearch Laboratories) at a 1:20000 dilution. Blots were incubated at RT for 5 min with Supersignal West Pico Chemiluminescent Substrate (Thermo Scientific) then exposed to film for 30 min.

Resistance Passaging

To determine the ability of *S. aureus* to generate resistance to the quorum quenching effects of 224C-F2, cultures were exposed to sub-MIC concentrations (16 µg mL$^{-1}$) of extract for 15 hrs, the OD$_{600}$ taken, and cultures centrifuged. The cell-free supernatant was removed and frozen for later HPLC quantification of δ-toxin. The cell pellets were then reconstituted in TSB to an OD equivalent of 5×10$^5$ CFU mL$^{-1}$ with extract (or vehicle control) added, and incubated while shaking as described above. This process was repeated for a total of 15 passaging days.

Biofilm Assay

Extract 224 and fractions were examined for impact on *S. aureus* biofilm formation using a human plasma protein-coated assay using strains UAMS-1 (a PFGE USA200 osteomyelitis isolate, agr type III) and its isogenic sarA mutant, UAMS-929, which has a biofilm deficient phenotype and serves as a positive control. the natural product-based anti-biofilm composition "220D-F2" was also included which inhibits biofilm formation in both *Staphylococcus aureus* and *Streptococcus pneumoniae*, as a positive drug control. Following inoculation and addition of appropriate media (containing extract or vehicle alone), 96-well plates (Falcon 35-1172) were incubated for 22 hrs at 37° C. The wells were gently washed with phosphate-buffered saline (PBS), fixed with ethanol, stained with crystal violet, rinsed in tap water, and the stain eluted into ethanol and transferred to a new plate prior to quantification of the eluate at an OD$_{595}$ with a Cytation™ 3 multimode plate reader (Biotek).

Mice and *S. aureus* Skin Infection Model

C$_5$Bl/6 dams were purchased from Charles Rivers (Wilmington, Mass.). Mice were allowed to acclimate to the BSL-2 level animal housing facility at the University of Iowa (Iowa City, Iowa) for at least seven days, prior to their inclusion in this study. All animal work described herein was approved by and conducted in accordance with the recommendations of Animal Care and Use Committee at the University of Iowa (IACUC #1205097). At D0, 8-12 week old mice were anesthetized with isoflurane, abdominal skin was carefully shaved with an Accu-Edge microtome blade (Sakura-Finnetek, Torrance, Calif.) and exposed skin was cleansed by wiping with an alcohol prep pad (Covidien, Mansfield, Mass.). For inoculum preparation, a USA 300 MRSA strain (AH1263) or its deletion mutant (AH1292) were grown in TSB medium overnight at 37° C. in a shaking incubator set to 200 rpm. Log-phase bacteria were obtained after a 2 hr subculture of a 1:100 dilution of the overnight culture in TSB. Bacterial cells were pelleted and resuspended in DPBS to a concentration of $1\times10^8$ CFUs/45 µL. 50 µL inoculum suspensions containing $1\times10^8$ CFUs and either 224C-F2 (5 µg, or 50 µg diluted in DMSO) or DMSO alone were injected to intradermally into abdominal skin using 0.3 mL/31 gauge insulin syringe (BD, Franklin Lakes, N.J.). Infectious dose was confirmed by plating serial dilutions of inoculum on TSA and counting ensuing colonies after overnight culture. Baseline body weights of mice were measured before infection and every day thereafter for a period of 7 days. For determination of lesion size, digital photos of skin lesions were taken daily with a Canon Rebel Powershot (ELPH 330 HS) and analyzed via ImageJ software (National Institutes of Health Research Services Branch, Bethesda, Md., USA).

224C-F2 Inhibits *S. aureus* Quorum Sensing Across the Diversity of agr Alleles.

A number of in vitro assays were employed to guide fractionation of the natural product composition and to evaluate efficacy in blocking *S. aureus* quorum sensing mediated virulence. Growth inhibitory impact of the extracts was assessed with traditional static MIC assays (Table 2); growth inhibition was also tracked in the fluorescent reporter assays for agr activity (FIG. 3).

Table 2. Growth and biofilm inhibition studies. Minimum inhibitory concentrations (MIC) were determined for extracts 224, 224C, 224C-F2 and control antibiotics (Ampicillin and Kanamycin) against *Staphylococcus aureus* strains. Minimum biofilm inhibiting concentration (MBIC) determination is also presented, and compared to control extract 220D-F2. All MIC and MBIC values are represented in µg mL$^{-1}$.

| | | Test Agent (µg mL$^{-1}$) | | | | | |
|---|---|---|---|---|---|---|---|
| Strain ID | MIC | 224 | 224C | 224C-F2 | Amp | Kan | 220D-F2 |
| AH430 | MIC$_{50}$ | 64 | 64 | 64 | 0.0625 | 2 | — |
| | MIC$_{90}$ | ND | ND | ND | 0.125 | 4 | — |
| AH1677 | MIC$_{50}$ | 32 | 16 | 64 | ND | ND | — |
| | MIC$_{90}$ | ND | ND | 256 | ND | ND | — |
| AH1747 | MIC$_{50}$ | 128 | 16 | 8 | ND | 1 | — |
| | MIC$_{90}$ | ND | ND | 256 | ND | 2 | — |
| AH1872 | MIC$_{50}$ | 16 | 64 | 16 | 4 | 1 | — |
| | MIC$_{90}$ | ND | ND | 128 | 8 | 4 | — |
| NRS385 | MIC$_{50}$ | 16 | 16 | 16 | ND | ND | — |
| | MIC$_{90}$ | ND | ND | 128 | ND | ND | — |
| UAMS-1 | MIC$_{50}$ | 32 | 64 | 32 | ND | 2 | 128 |
| | MIC$_{90}$ | ND | ND | ND | ND | 4 | ND |
| | MBIC$_{50}$ | 200 | 100 | 200 | — | — | 12.5 |
| | MBIC$_{90}$ | ND | ND | 400 | — | — | 100 |

224C-F2 Blocks *S. aureus* Damage to Human Keratinocytes

Figure 5:
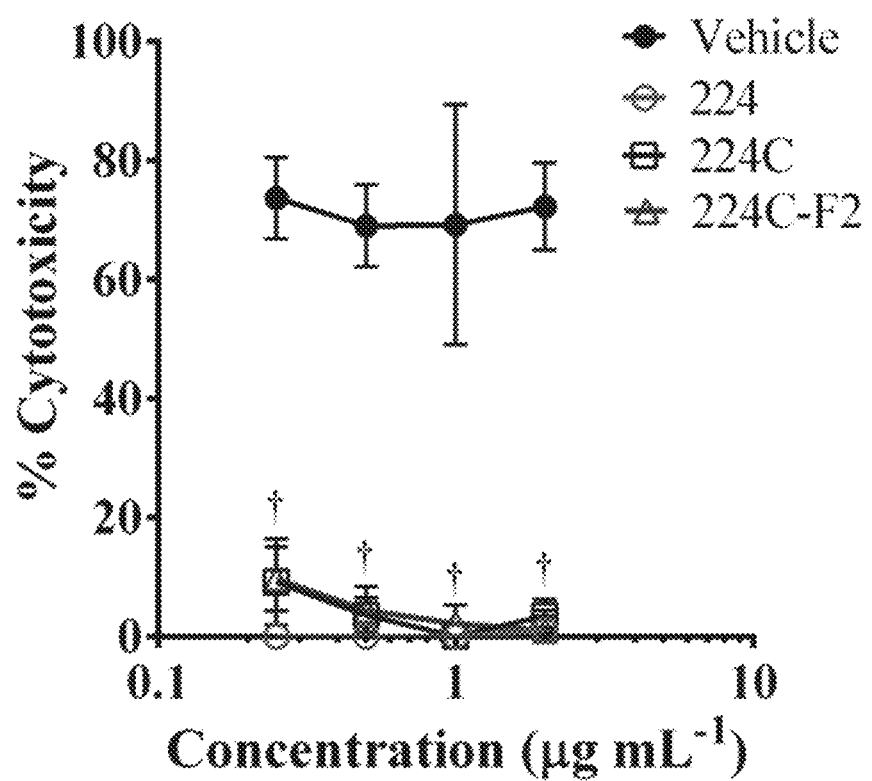
FIG. 5 shows data where spent supernatants of *S. aureus* treated with 224C-F2 exhibit diminished cytotoxic effects against human keratinocytes. Supernatants were applied to HaCaT cells (20% v/v for 24 hrs) to measure the lytic capacity (determined by LDH assay) of a full suite of *S. aureus* exotoxins. Supernatants from 224C-F2-treated cultures were non-toxic to the mammalian cells, confirming inhibition of exotoxin production.

In addition to monitoring the activity of each agr allele and detecting specific downstream products (e.g. α-hemolysin and δ-toxin), virulence impact data was captured on other exotoxins that could be produced through this system. To do this, HaCaT cells were exposed to the sterile-filtered supernatants of treated and control cultures. The difference in cytotoxicity as detected by LDH assay was clear (p<0.001) for all extracts (224, 224C, and 224C-F2) in comparison to control, and this was evident at doses as low as 0.25 µg mL$^{-1}$ (FIG. 5A). Following exposure to supernatants (14% v/v for 3 hrs) or staurosporine (7.1 µM for 3 hrs), HaCaT cells were imaged by fluorescent microscopy to examine cell integrity. Images of the HaCaT cells following exposure to the supernatants reaffirmed the lack of exotoxins in the supernatants in 224C-F2 treated cultures.

Repeated Exposure to 224C-F2 does not Lead to Resistance

Antibiotic resistance is a major concern in any anti-infective drug discovery initiative. Here, it is hypothesized that targeting bacterial virulence with a multi-component botanical therapy—potentially containing multiple actives acting on multiple targets—would not be very likely to generate resistance. As reporter strains can lose their effectiveness in tracking activity over multiple passaging days (e.g. due to loss of the plasmid), a method was designed for tracking the quorum quenching efficacy of the composition (224C-F2). This was achieved through use of a high toxin output strain (NRS385) that consistently produces high levels of δ-toxin in the supernatant. Bacterial growth was monitored by OD$_{600}$ and δ-toxin was quantified by HPLC. Data for total peak area measured by HPLC (FIG. 6A) and area adjusted for slight differences in daily OD (FIG. 6B) both reflect significant differences between the levels of δ-toxin produced by the treated versus control cultures for 15 days of passaging. Moreover, no trends in the shift of this observation towards resistance were noted.

224C-F2 is Nontoxic to HaCaT Cells and Mouse Skin

Figure 7:
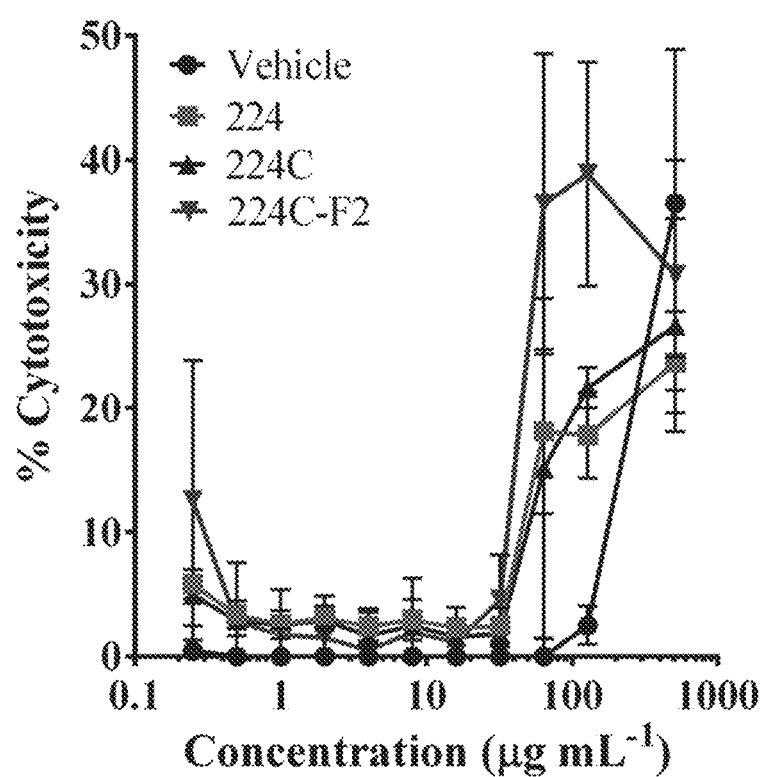
FIG. 7 shows data indicating 224C-F2 is non-toxic to human keratinocytes and murine skin. Immortalized human keratinocytes (HaCaT cells) were treated with up to 512 µg mL$^{-1}$ of extract fractions (24 hrs). The LD$_{50}$ for 224C-F2 could not be determined at this test range, indicating that it is well above the active dose for quorum quenching activity (IC$_{50}$=1.56-25 µg mL$^{-1}$, depending on strain). Uninfected mice received an intradermal injection of 5 or 50 µg 224C-F2. No gross alterations in skin appearance were observed.

To investigate the potential for cytotoxic or irritant effects of *C. sativa* leaf extracts, immortalized human keratinocyte cells were treated with up to 512 µg mL$^{-1}$ of each extract. In all cases (224, 224C, 224C-F2), cytotoxicity (>30%) was only observed at doses at 8-10 times greater than the dose range necessary for quorum quenching activity, and which also corresponded with the rise in toxicity of vehicle treatment alone (DMSO), with no significant difference in cytotoxicity between the vehicle and extracts (FIG. 7). With regards to the potential for irritant or necrotic effects on murine skin, mice were injected intradermally with either 5 µg or 50 µg and monitored for any visible changes in the skin morphology and weight loss. No changes were noted any day at up to 6 days of post-injection follow-up.

224C-F2 Attenuates MRSA-induced Illness in an in vivo Skin Infection Model

Figure 8A:
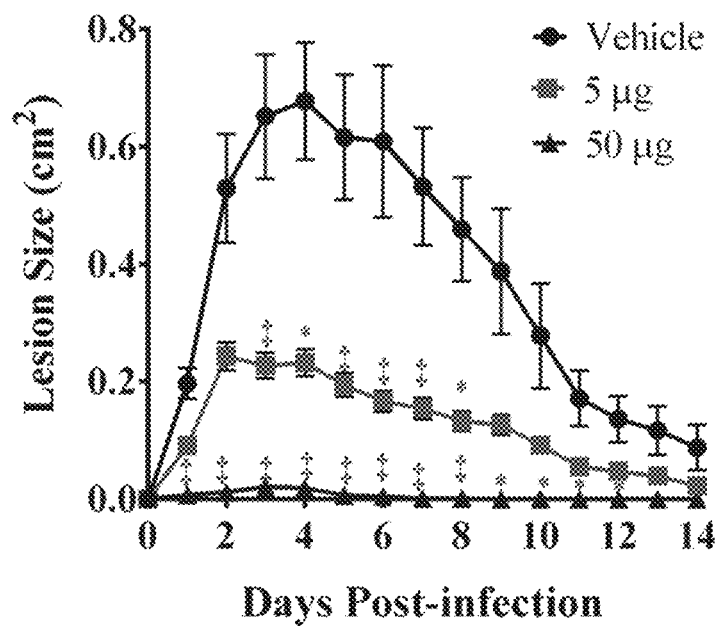
FIG. 8A shows data indicating 224C-F2 attenuates MRSA-induced dermatopathology in a murine model of skin and soft tissue infection. C5Bl/6 mice were intradermally injected with 1×10$^8$ CFUs of LAC (USA 300 isolate, AH1263) or its agr deletion mutant (AH1292). Mice received a single dose of 224C-F2 (at 5 or 50 µg) or the vehicle control (DMSO) at the time of infection. 224C-F2 attenuates dermatopathology with a single dose of either 5 or 50 µg.
Figure 8B:
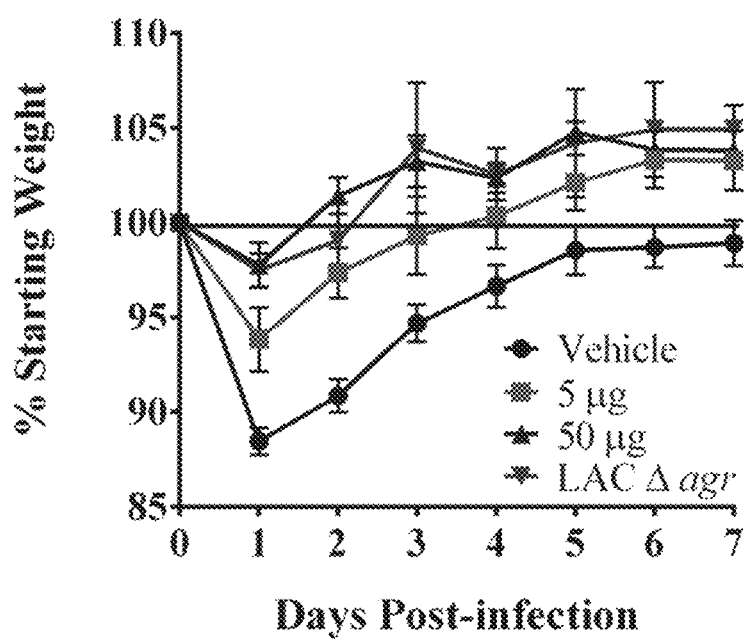
FIG. 8B shows data indicating 224C-F2 reduces morbidity and mice do not lose weight.

The agr quorum sensing system controls *staphylococcal* virulence factor expression and is required for necrotic skin lesion formation following cutaneous challenge. Having demonstrated the quorum sensing inhibiting activity of 224C-F2 in vitro (FIGS. 3-6), the efficacy of this composition was assessed in a mouse model of *S. aureus* skin infection. When delivered at the time of infection, 224C-F2 decreased the area of resultant ulcers in a dose-dependent manner (FIG. 8A). In addition, 224C-F2 administration significantly attenuated infection-induced morbidity (assessed by weight loss) compared to vehicle treated controls (FIG. 8B). Importantly, mice receiving intradermal injection of 224C-F2 alone did not exhibit any overt signs of dermal irritation or clinical illness e.g., weight loss, malaise, hunching, coat ruffling (FIG. 7). Together these data corroborate the in vitro findings and suggest that 224C-F2 impairs MRSA pathogenesis without manifesting local or systemic toxicity.

224C-F2 Activity Against *Propionibacterium acnes*

The extract 224C-F2 was tested for growth inhibitory activity against two strains of *Propionibacterium acnes*. Clindamycin was used as the positive control. The MIC, or minimum inhibitory concentration for growth is represented at MIC50 (or at 50% inhibition of the growth control) or MIC90 for 90% inhibition. Likewise, the MBEC, or minimum biofilm eradicating concentration, is represented at 50% (MBEC50) and 90% (MBEC90) of the mock vehicle control (DMSO or water).

| | | | Test Agent ($\mu g\ mL^{-1}$) | |
|---|---|---|---|---|
| Species | Strain ID | MIC | 224C-F2 | Clin |
| *Propionibacterium acnes* | HL005PA2 | $MIC_{50}$ | 128 | 0.0625 |
| | | $MIC_{90}$ | ND | 0.25 |
| *Propionibacterium acnes* | ATCC6919 | $MIC_{50}$ | 256 | 0.125 |
| | | $MIC_{90}$ | 256 | 0.125 |

In addition to testing 224C-F2, other crude extracts of *Castanea sativa* were also tested against *P. acnes* strain ATCC 6919, and also demonstrated activity:

| | Extraction | Extract | | Test Agent ($\mu g\ mL^{-1}$) | |
|---|---|---|---|---|---|
| Plant part | solvent | ID | MIC | Extract | Clin |
| Leaves | MeOH | 224 | $MIC_{50}$ | 256 | 0.125 |
| | | | $MIC_{90}$ | — | 0.125 |
| Leaves with gall structures | MeOH | 226 | $MIC_{50}$ | 256 | 0.125 |
| | | | $MIC_{90}$ | — | 0.125 |

These studies demonstrate that extracts of *Castanea sativa* leaves exhibit growth inhibitory activity against *Propionibacterium acnes* and could hold potential utility in formulations for the treatment of acne flares.

Chemical Characterization of 224C-F2

Figure 2A:
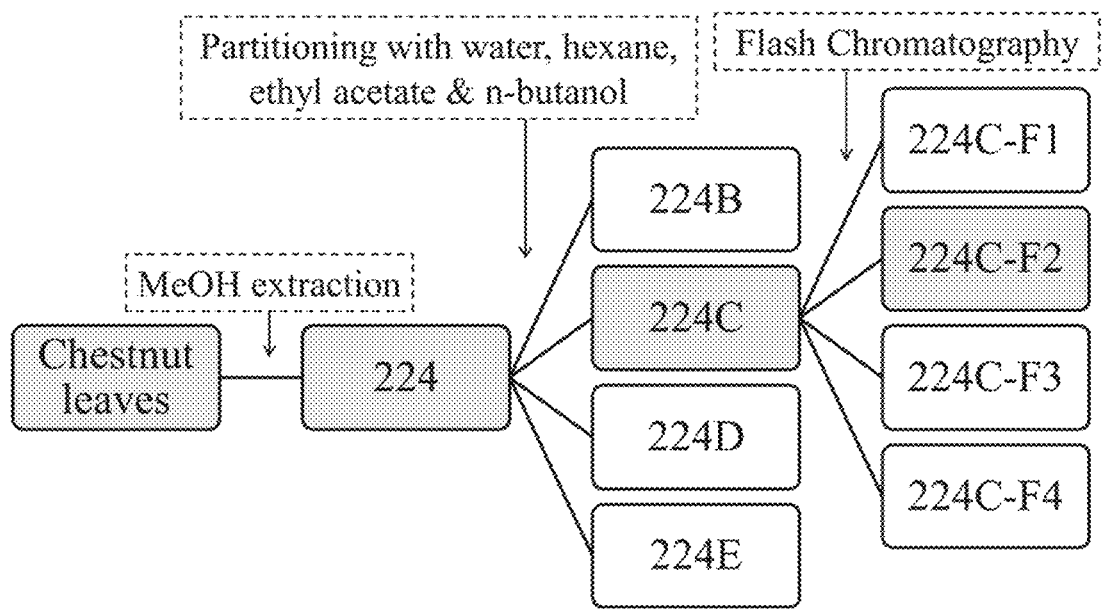
FIG. 2A shows an extract isolation scheme. The bioassay-guided fractionation scheme is illustrated, demonstrating the path from raw plant material to isolated, active natural products.
Figure 2B:
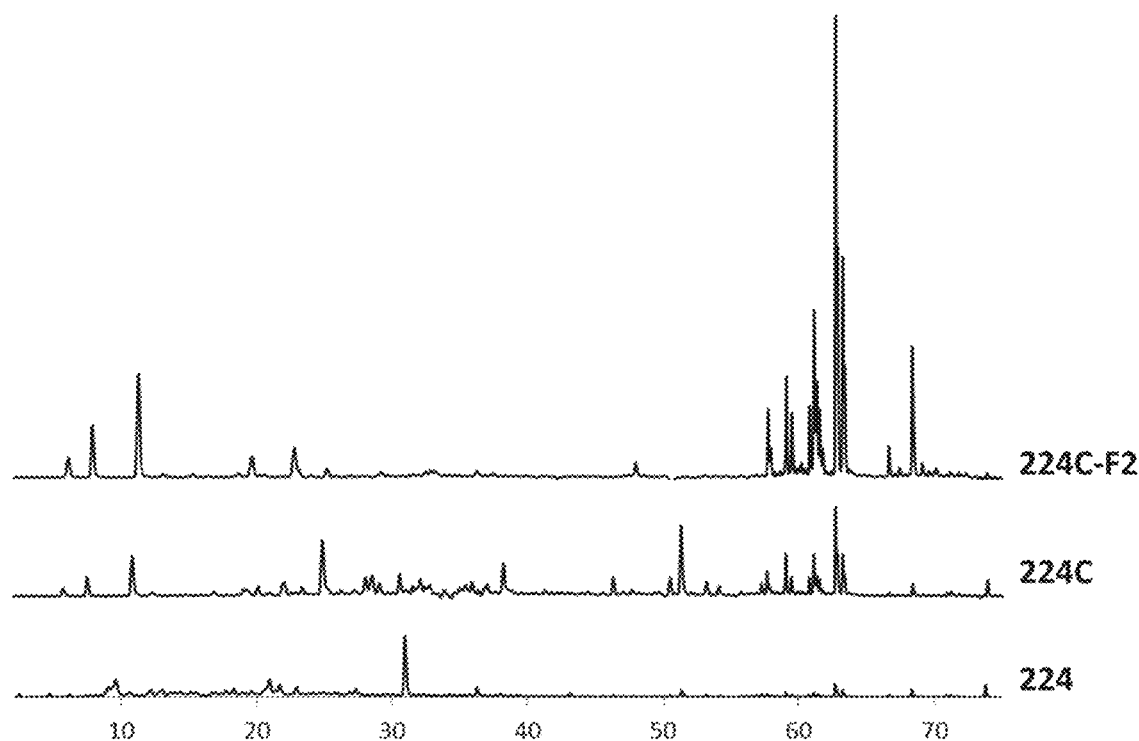
FIG. 2B shows overlapping HPLC chromatogram for the most active fractions corresponding to FIG. 2A illustrating how fractionation functions to increase the relative levels of active agents.
Figure 3A:
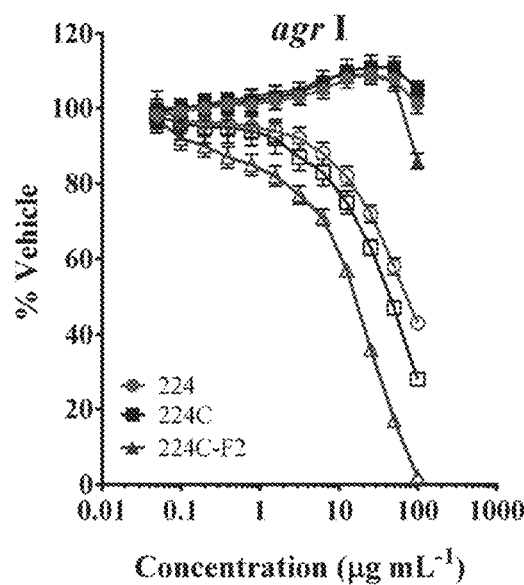
FIG. 3A shows data indicating chestnut leaf extracts inhibit for agr I, strain AH1677, in a non-biocide manner. *S. aureus* agr reporter strains were treated with extracts 224, 224C, and 224C-F2 at a dose range of 0.05-100 µg mL$^{-1}$. Bioactivity guided sequential fractionation resulted in increased quenching of all 4 agr alleles in a manner independent of growth inhibition. Optical density of the culture is represented by solid black symbols; fluorescence in the agr reporters is indicated by the open symbols. The $IC_{50}$ and $IC_{90}$ for quorum quenching impact of each extract are reported in Table 3
Figure 3B:
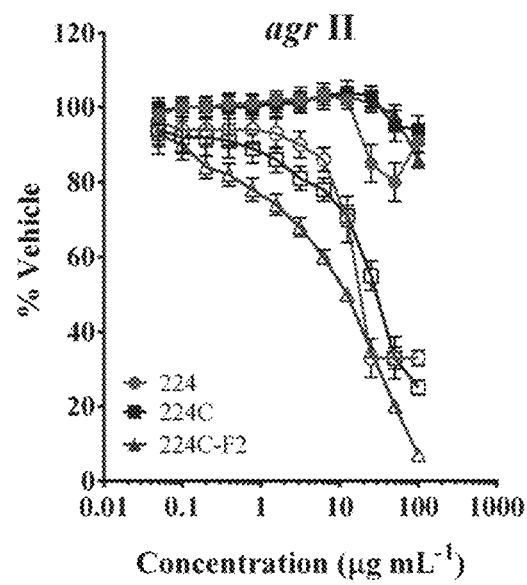
FIG. 3B shows data for agr II, strain AH430, as in FIG. 3A.
Figure 3C:
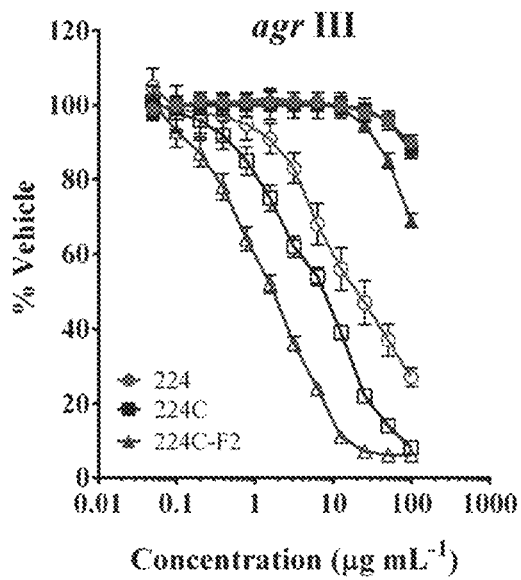
FIG. 3C shows data for agr III, strain AH1747, as in FIG. 3A.
Figure 3D:
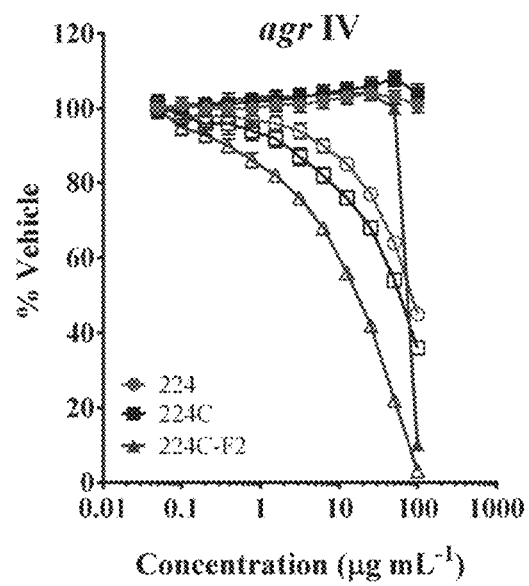
FIG. 3D shows data for agr IV, strain AH1872, as in FIG. 3A.

The percent yield of extract from the dry leaves was 43.98% for extract 224, 2.716% for 224C and 1.155% for 224C-F2 (FIG. 2). LC-FTMS analysis of 224C-F2 revealed the presence of at least 94 compounds (Table 4).

TABLE 4

Figure 9A:
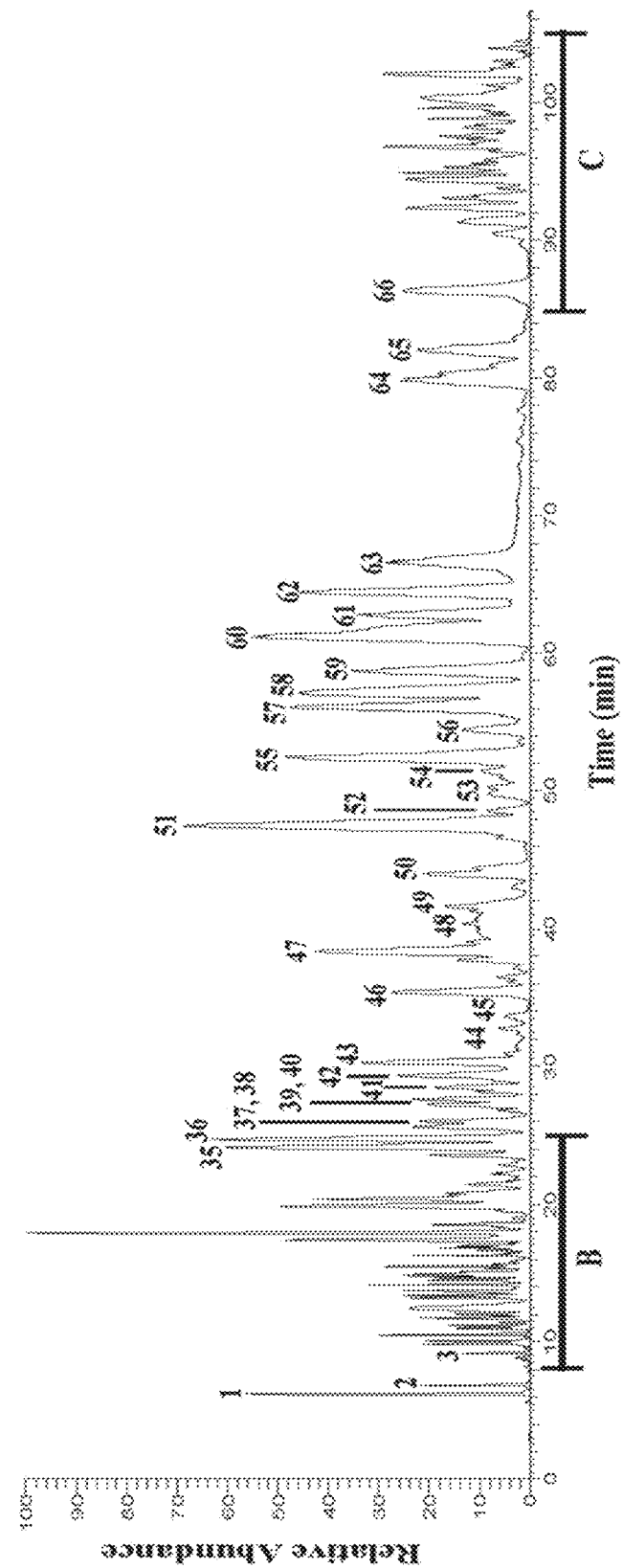
FIG. 9A LC-FTMS ESI negative base peak chromatogram for 224C-F2. Peaks correspond to data presented in Table 4. Putative structures are reported in FIG. 10.
Figure 9B:
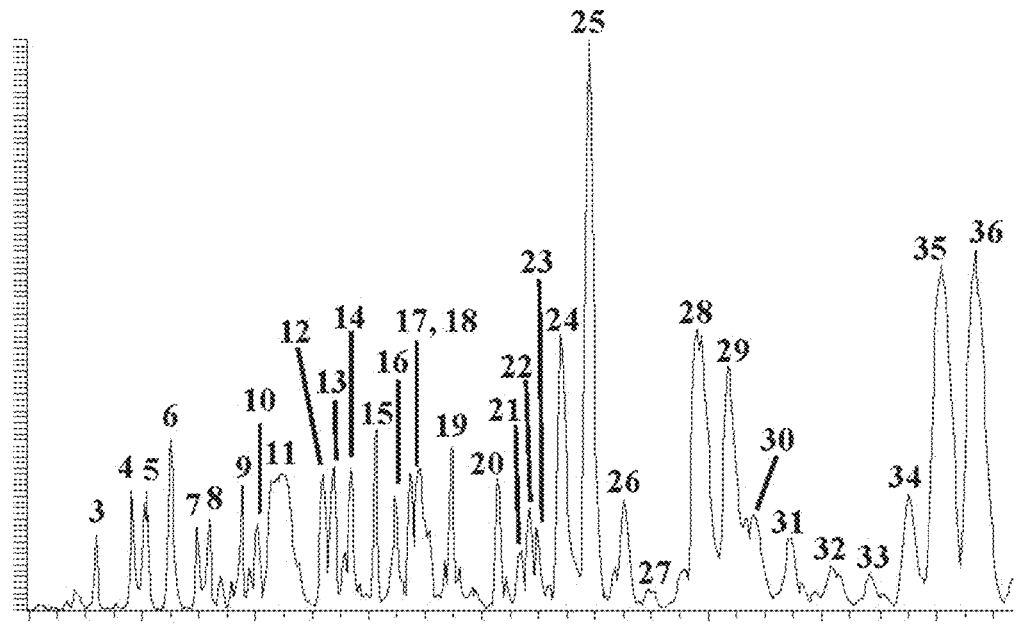
FIG. 9B shows an expansion of the B segment provided in FIG. 9A.
Figure 9C:
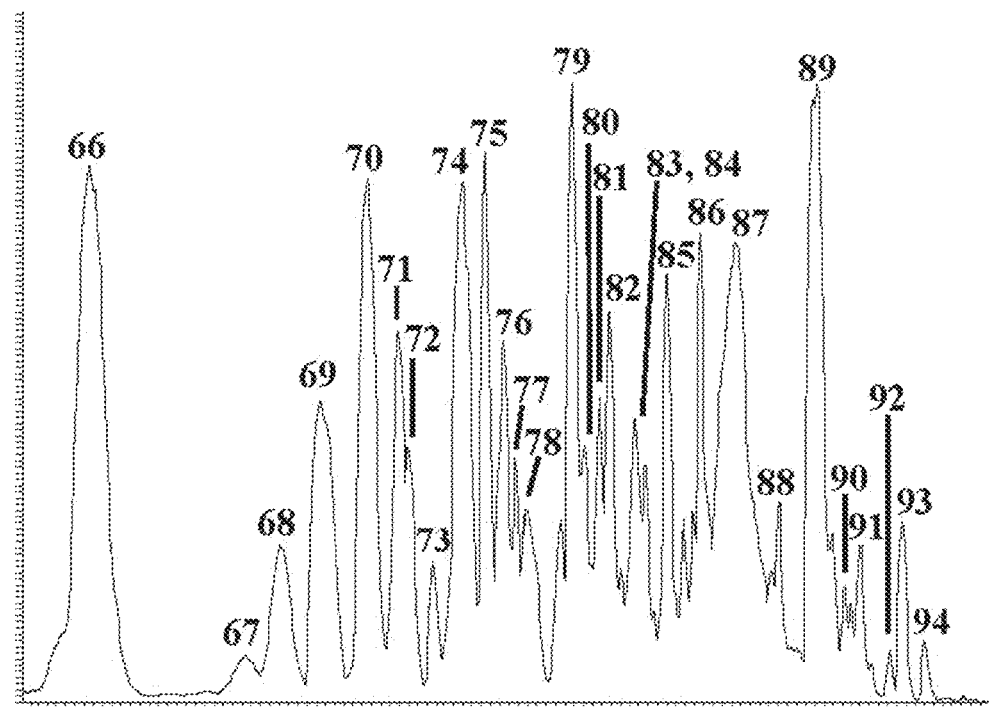
FIG. 9C shows an expansion of the C segment provided in FIG. 9A.
Figure 11:
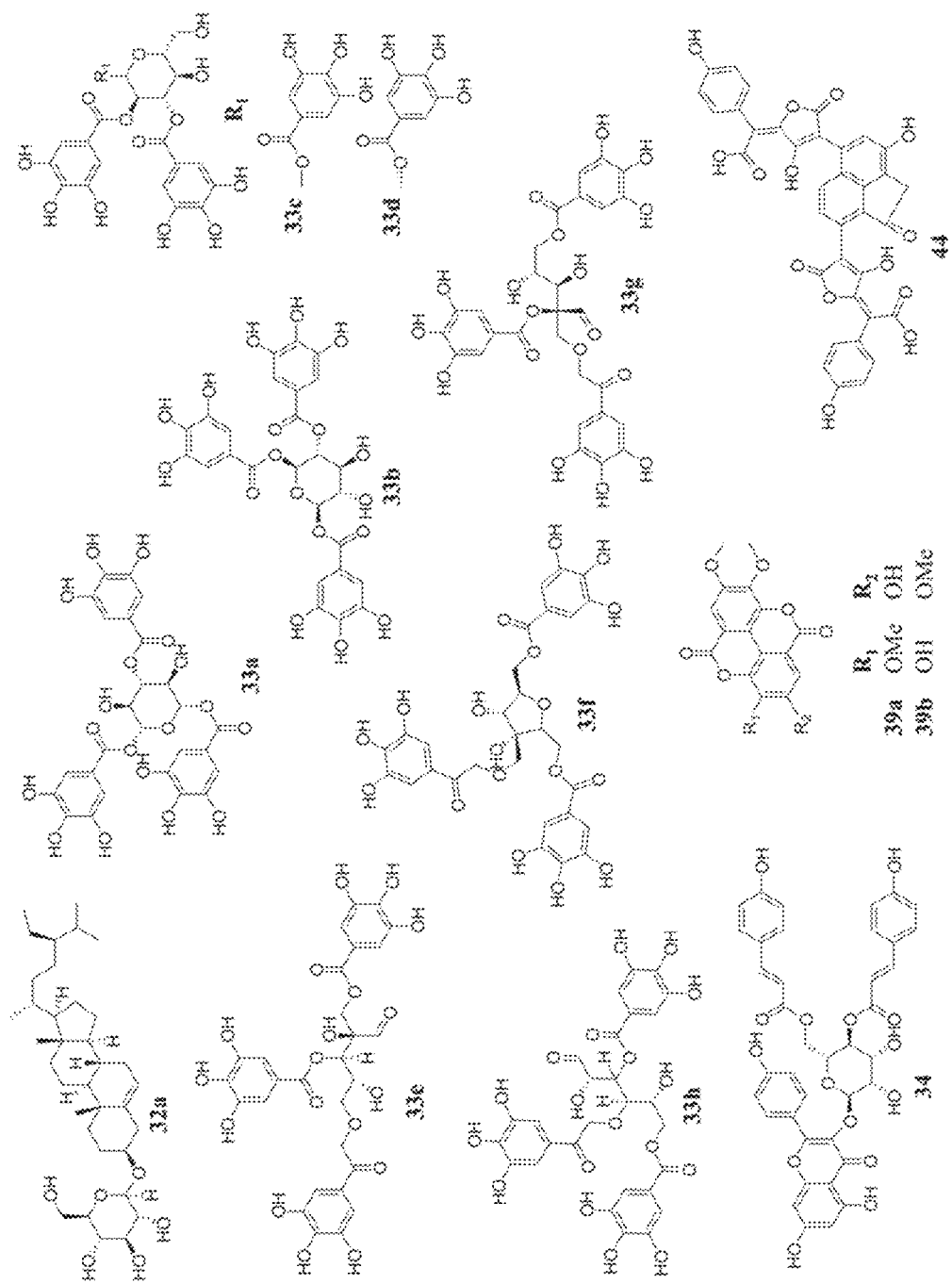
FIG. 11 shows putative structures of compounds other than pentacyclic triterpenes found in the most active region of 224C-F2 (retention time of 21-49 min). Compounds are listed by peak number, corresponding to Table 4. Peak 32 was determined to be $C_{35}H_{59}O_6$ with a relative abundance of 0.30%. Putative structural matches include: (32a) stigmastane and (32b) (3β,4β,16α, 21β,22α)-16,21,22,23,28-pentamethoxy (9CI) olean-12-en-3-ol (FIG. 10). Peak 33 was determined to be $C_{27}H_{23}O_{18}$ with a relative abundance of 0.16%. Putative structural matches include: (33a) 1,3,6-tri-O-galloylglucose; (33b) 1,2,6-tri-galloyl-β-D-glucose; (33c) 1,2,3-tri-O-galloylglucose; (33d) 1,2,3-tri-O-galloyl-β-D-glucopyranose; (33e) 2',3,5-tri-O-galloyl-D-hamamelose; (33f) 2-C-[[(3,4,5-tri hydroxybenzoyl)oxy]methyl]-1,5-bis (3,4,5-trihydroxybenzoate) D-Ribofuranose; (33g) kurigalin; (33h) 3,4,6-tri-O-galloyl-D-glucose. Peak 34 was determined to be $C_{39}H_{31}O_{15}$ with a relative abundance of 0.65%. Putative structural matches include: (34) castanoside B. Peak 39 was determined to be $C_{17}H_{11}O_8$ or $C_{20}H_{11}O_4N_2$ with a relative abundance of 0.72%. Putative structural matches include: (39a) 3,4,3'-tri-O-methylellagic acid and (39b) 3,3',4'-tri-O-methylellagic acid. Peak 44 was determined to be $C_{34}H_{29}O_{15}$ with a relative abundance of 0.26%. Putative structural matches included (44) norbadione A.

Mass spectrometry (m/z) analysis of 224C-F2. The corresponding chromatogram is reported in FIG. 9; putative structures in FIG. 10 and 11.

| Peak No. | Retention Time (min) | Relative Abundance | Formula (Δ ppm) | m/z* ([M − H]$^-$ in bold) | $MS^2$ | UV |
|---|---|---|---|---|---|---|
| 1 | 6.21 | 0.99 | $C_{14}H_9O_{10}$ (0.950) | 337.02044, 675.05002 | 293.2077 | 220, 270 |
| 2 | 6.85 | 0.39 | $C_{14}H_{11}O_{10}$ (0.586) | 339.0354 | 169.104 | 220, 270 |
| 3 | 9.17 | 0.12 | $C_{14}H_9O_8$ (1.993) | 305.03035, 611.06804 | 179.1553 | ND |
| 4 | 9.82 | 0.24 | $C_{14}H_9O_9$ (2.347) | 321.02541, 643.05813 | 169.1691 | 215, 280 |
| 5 | 10.05 | 0.32 | $C_{31}H_{17}O_{15}N$ (0.313) | 321.02581, 579.15259, 611.10667, 643.06011 | 599.13610, 626.17633 | 215, 280 |
| 6 | 10.49 | 0.36 | $C_8H_7O_5$ (2.031) | 183.02972, 367.06658 | 124.08116, 168.05430, 183.09955 | 215, 275 |
| 7 | 10.94 | 0.14 | $C_{14}H_9O_9$ (2.097) | 321.02533, 643.05801 | 169.1772 | ND |
| 8 | 11.18 | 0.16 | $C_{18}H_{15}O_8$ (2.138) | 33.06169, 359.07746 | 179.1279 | 215, 325 |
| 9 | 11.74 | 0.22 | $C_{21}H_{25}O_8$ (1.898) | 405.15626, 451.23452, 521.24023 | 225.224 | ND |
| 10 | 12.02 | 0.19 | $C_{25}H_{39}O_7$ (1.337) | 269.13963, 451.27073 | 407.24461, 433.23288 | ND |
| 11 | 12.39 | 1.24 | $C_{28}H_{11}O_{16}$ (2.757) | 603.0069 | 465.2773 | 255, 365 |
| 12 | 13.18 | 0.33 | $C_{15}H_{11}O_9$ (1.537) | 335.04137, 671.08973 | 183.209 | ND |
| 13 | 13.36 | 0.32 | $C_{29}H_{33}O_{10}$ (2.420) | 421.15146, 541.20923 | 491.18281, 523.30375 | ND |
| 14 | 13.68 | 0.33 | $C_{15}H_{11}O_9$ (1.358) | 335.04131, 671.09010 | 183.1594 | 215, 280, 305 (s) |
| 15 | 14.13 | 0.33 | $C_{12}H_{19}O_5$ (1.329) | 243.12412, 487.25602 | 225.1935 | ND |
| 16 | 14.47 | 0.30 | $C_{12}H_{19}O_5$ (1.288) | 243.12411, 487.25527 | 181.17663, 183.17220, 199.20072, 225.24659 | ND |
| 17 | 14.71 | 0.26 | $C_{23}H_{23}O_5N_4$ (−0.076) | 435.1674 | 259.15392, 388.97603 | ND |
| 18 | 14.90 | 0.54 | $C_{33}H_{13}O_{13}N$ (0.081) | 391.14110, 631.03874 | 479.4478 | 220, 255 (s), 320 |

TABLE 4-continued

Mass spectrometry (m/z) analysis of 224C-F2. The corresponding chromatogram is reported in FIG. 9; putative structures in FIG. 10 and 11.

| Peak No. | Retention Time (min) | Relative Abundance | Formula ($\Delta$ ppm) | m/z* ([M − H]− in bold) | MS$^2$ | UV |
|---|---|---|---|---|---|---|
| 19 | 15.44 | 0.32 | $C_{20}H_{31}O_8$ (2.101) | 399.2033 | 381.33071, 355.30539, 337.33447 | ND |
| 20 | 16.26 | 0.25 | $C_{30}H_{39}O_8$ (2.046) | 527.2661 | 263.20418, 459.45849 | ND |
| 21 | 16.63 | 0.16 | $C_{59}H_{41}O$ (−1.084) | 405.15614, 765.31542 | 613.37801, 617.27520 | ND |
| 22 | 16.84 | 0.21 | $C_{25}H_{23}O_{13}$ (1.179) | 599.1065 | 255.10369, 284.12921, 285.12352, 327.22129, 471.26204 | ND |
| 23 | 16.97 | 0.17 | $C_{15}H_9O_6$ (0.873) | 285.04071, 571.08859 | 175.11613, 199.13418, 241.14281 | ND |
| 24 | 17.39 | 1.15 | $C_{15}H_9O_7$ (1.907) | 301.03595, 603.08092, 905.12920 | 151.08622, 179.07130 | 215, 255, 370 |
| 25 | 17.88 | 2.08 | $C_{18}H_{31}O_5$ (1.414) | 327.21816, 655.44500 | 211.20899, 229.25489, 291.32982 | 220, 280, 330 |
| 26 | 18.50 | 0.40 | $C_{26}H_{39}O_6$ (1.918) | 447.27607, 493.28185, 895.56483 | 367.44245, 385.41613, 401.41446, 429.40811 | ND |
| 27 | 18.97 | 0.08 | $C_{25}H_{23}O_{13}$ (1.461) | 519.33352, 531.11519, 564.33918 | 471.23936, 489.30998 | ND |
| 28 | 19.81 | 1.90 | $C_{43}H_{65}O_{24}$ (−0.265) | 329.23393, 635.14327, 965.38687 | 635.3972 | 220, 270, 315 |
| 29 | 20.33 | 1.31 | $C_{50}H_{19}O$ (−1.840) | 635.143 | 285.15142, 489.24712, 575.28563 | ND |
| 30 | 20.79 | 0.50 | $C_{18}H_{31}O_5$ (1.842) | 327.21830, 655.44361 | 171.19486, 309.30290 | ND |
| 31 | 21.45 | 0.34 | $C_{39}H_{59}O_8$ (34.188); $C_{38}H_{55}O_9$ (89.700) | 327.21808, 635.14199, 655.44397 | 611.57685, 637.50026 | 220, 345 |
| 32 | 22.15 | 0.30 | $C_{35}H_{59}O_6$ (39.112) | 287.22306, 327.21853, 419.16528, 575.45419, 661.36183, 755.16549 | 515.51088, 531.44821, 557.36796 | 220, 365 |
| 33 | 22.76 | 0.16 | $C_{27}H_{23}O_{18}$ (80.837) | 327.21797, 635.1404 | 285.14949, 489.26353 | 220, 315 |
| 34 | 23.54 | 0.65 | $C_{39}H_{31}O_{15}$ (1.118) | 739.1677 | 285.14592, 453.23143 | 220, 270, 315 |
| 35 | 24.11 | 2.67 | $C_{57}H_{23}O_2$ (−1.263) | 739.16945, 785.17519 | 285.13965, 453.25508, 575.28574, 593.30977 | 220, 315 |
| 36 | 24.70 | 2.65 | $C_{27}H_{41}O_6$ (2.250) | 461.29190, 507.29838, 923.59481 | 399.45155, 415.44332, 443.44095 | ND |
| 37 | 25.61 | 0.90 | $C_{57}H_{23}O_2$ (−1.520) | 739.16923, 785.17625 | 285.14029, 453.24568, 575.300080, 593.27713 | 220, 315 |
| 38 | 26.00 | 0.84 | $C_{55}H_{21}ON_3$ (−0.163) | 739.16895, 785.17576 | 285.14254, 453.25317, 575.30248, 593.29857 | 220, 315 |
| 39 | 27.18 | 0.72 | $C_{17}H_{11}O_8$ (3.317); $C_{20}H_{11}O_4N_2$ (75.038) | 343.04651, 687.10014 | 328.2618 | 225, 370 |
| 40 | 27.57 | 0.84 | $C_{40}H_{27}O_{11}N_4$ (0.026) | 739.1683 | 285.15812, 453.24020, 575.26598, 593.28341 | ND |

TABLE 4-continued

Mass spectrometry (m/z) analysis of 224C-F2. The corresponding chromatogram is reported in FIG. 9; putative structures in FIG. 10 and 11.

| Peak No. | Retention Time (min) | Relative Abundance | Formula (Δ ppm) | m/z* ([M − H]⁻ in bold) | MS² | UV |
|---|---|---|---|---|---|---|
| 41 | 28.45 | 0.68 | $C_{34}H_{29}O_{15}$ (0.822) | 677.15166, 723.15962 | 284.13571, 557.27766, 617.28692 | 220, 310 |
| 42 | 29.30 | 1.43 | $C_{31}H_{49}O_6$ (−68.377) | 517.31804, 563.32400, 723.15771, 797.17555, 1035.64788 | 437.46551, 455.47822 | ND |
| 43 | 30.28 | 1.86 | $C_{30}H_{45}O_7$ (2.500) | 517.31837, 563.32368, 1035.64687 | 437.46548, 455.47972, 499.50877 | ND |
| 44 | 32.74 | 0.26 | $C_{34}H_{29}O_{15}$ (−1.423) | 677.1506 | 285.14940, 531.27599, 617.30259 | ND |
| 45 | 33.59 | 0.31 | $C_{34}H_{29}O_{15}$ (−1.112) | 547.32815, 677.15045 | 285.1559, 531.29170 | ND |
| 46 | 35.37 | 1.64 | $C_{57}H_{23}O_2N_3$ (−0.557) | 781.17897, 827.18606 | 285.14510, 495.29220, 617.28374, 635.31959 | 225, 310 |
| 47 | 38.38 | 3.13 | $C_{57}H_{23}O_2N_3$ (0.288) | 781.17980, 827.18720 | 285.14324, 495.26366, 635.32730 | 220, 315 |
| 48 | 40.35 | 1.45 | $C_{59}H_{25}O_3$ (−0.676) | 445.29698, 491.30248, 781.18038, 827.18746, 1227.49773 | 285.14614, 496.26557, 635.31187 | 220, 285, 310 |
| 49 | 41.60 | 1.07 | $C_{59}H_{25}O_3$ (−1.201) | 533.34940, 781.18002, 827.18679 | 285.12660, 495.27804, 635.31517 | 220, 305 |
| 50 | 43.97 | 1.20 | $C_{41}H_{33}O_{16}$ (0.617) | 781.1779 | 285.13183, 495.28281, 635.30008 | 220, 295 |
| 51 | 47.42 | 5.96 | $C_{30}H_{47}O_5$ (2.221) | 487.34398, 533.35098, 975.70011 | 469.4979 | ND |
| 52 | 48.55 | 0.48 | $C_{32}H_{51}O_7$ (−0.543) | 547.36365, 593.36950 | 529.51760, 529.51407 | ND |
| 53 | 49.73 | 0.93 | $C_{31}H_{49}O_7$ (−1.063) | 533.3478 | 435.49468, 486.52688, 515.46714 | ND |
| 54 | 51.40 | 0.67 | $C_{30}H_{47}O_5$ (−0.508) | 487.34265, 533.34807 | 485.22061, 486.02828, 487.97113 | ND |
| 55 | 52.42 | 4.11 | $C_{30}H_{47}O_5$ (2.262) | 487.34400, 533.35101, 975.70046 | 469.499 | 225, 270 |
| 56 | 54.43 | 0.97 | $C_{31}H_{49}O_8$ (2.418) | 531.33301, 549.34462 | 489.57421, 531.41583 | ND |
| 57 | 56.01 | 3.84 | $C_{30}H_{47}O_5$ (2.385) | 487.34406, 533.35100, 975.70018 | 441.51916, 469.49007 | ND |
| 58 | 57.15 | 4.36 | $C_{59}H_{25}O_3N_3$ (−0.498) | 823.18973, 869.19736 | 285.13804, 677.32656 | 225, 315 |
| 59 | 58.72 | 2.88 | $C_{59}H_{25}O_3N_3$ (−0.668) | 823.18959, 869.19629 | 285.14787, 677.31854 | 220, 315 |
| 60 | 61.17 | 6.80 | $C_{30}H_{47}O_6$ (2.359) | 503.33900, 549.34625, 1007.69059 | 471.4702 | ND |
| 61 | 62.79 | 2.56 | $C_{59}H_{25}O_3N_3$ (−0.790) | 823.18949, 869.19646 | 285.13196, 677.32432 | 220, 315 |
| 62 | 64.42 | 3.63 | $C_{59}H_{25}O_3N_3$ (−1.020) | 823.1893 | 285.12941, 677.31768 | 220, 315 |
| 63 | 66.55 | 3.09 | $C_{30}H_{47}O_6$ (1.783) | 503.33871, 549.34568, 1007.69071 | 319.32486, 401.40810, 471.48019 | ND |
| 64 | 79.78 | 2.91 | $C_{30}H_{45}O_5$ (2.930) | 485.32867, 531.33501, 971.66969 | 423.49110, 467.49405 | ND |
| 65 | 81.93 | 1.98 | $C_{30}H_{49}O_5$ (1.517) | 489.35929, 535.36558, 979.72844 | 471.5105 | ND |

TABLE 4-continued

Mass spectrometry (m/z) analysis of 224C-F2. The corresponding chromatogram is reported in FIG. 9; putative structures in FIG. 10 and 11.

| Peak No. | Retention Time (min) | Relative Abundance | Formula (Δ ppm) | m/z* ([M − H]⁻ in bold) | MS² | UV |
|---|---|---|---|---|---|---|
| 66 | 86.29 | 2.25 | $C_{27}H_{41}O_5$ (1.151) | 445.29464, 491.30202, 891.60136 | 383.45557, 427.42744 | ND |
| 67 | 89.69 | 0.13 | $C_{31}H_{49}O_7$ (−0.744) | 533.348 | 487.4407 | ND |
| 68 | 90.42 | 0.46 | $C_{31}H_{51}O_6$ (−1.179) | 519.3685 | 415.49682, 487.52239 | ND |
| 69 | 91.30 | 0.92 | $C_{39}H_{53}O_7$ (0.273) | 633.37985, 679.38594 | 179.08913, 454.54671, 590.61801 | 225, 295, 305 |
| 70 | 92.33 | 1.20 | $C_{32}H_{49}O_6$ (1.998) | 529.35452, 575.36114, 1059.72276 | 469.5822 | ND |
| 71 | 92.99 | 0.51 | $C_{32}H_{49}O_6$ (2.281) | 529.35467, 575.36044 | 469.6057 | ND |
| 72 | 93.19 | 0.31 | $C_{27}H_{43}O_4$ (3.842) | 431.31834, 477.32329, 529.35529 | ND | ND |
| 73 | 93.74 | 0.16 | $C_{40}H_{55}O_9$ (0.447) | 547.36537, 679.38546 | 619.46845, 661.52463 | ND |
| 74 | 94.38 | 1.26 | $C_{53}H_{99}O_{13}$ (1.032) | 471.35048, 517.35526, 943.71008 | 471.52443, 925.86052 | ND |
| 75 | 94.85 | 0.69 | $C_{39}H_{53}O_7$ (2.957) | 633.3816 | 470.54105, 514.52351, 590.59043 | ND |
| 76 | 95.27 | 0.47 | $C_{32}H_{49}O_6$ (2.583) | 529.35483, 575.36059 | 469.5901 | ND |
| 77 | 95.52 | 0.18 | $C_{32}H_{49}O_7$ (2.022) | 545.34949, 591.35525 | 485.4473 | ND |
| 78 | 95.80 | 0.40 | $C_{33}H_{45}ON$ (−1.238) | 471.35008, 517.35387, 943.70544 | ND | ND |
| 79 | 96.74 | 0.82 | $C_{32}H_{49}O_7$ (2.169) | 545.34956, 591.35536 | 453.49263, 485.45412, 513.44457 | ND |
| 80 | 97.00 | 0.25 | $C_{31}H_{49}O_7$ (1.487) | 485.32855, 533.34917, 591.35511 | 489.44583, 513.21950 | ND |
| 81 | 97.34 | 0.29 | $C_{32}H_{49}O_7$ (1.564) | 545.34923, 591.35526 | 485.4417 | ND |
| 82 | 97.56 | 0.44 | $C_{33}H_{45}ON$ (−3.677) | 471.34893, 517.35439 | 453.5104 | ND |
| 83 | 98.10 | 0.39 | $C_{48}H_{59}O_{10}$ (−0.982) | 795.4106 | 633.6017 | 225, 300, 325 |
| 84 | 98.33 | 0.23 | $C_{48}H_{59}O_{10}$ (0.351) | 485.32931, 531.33456, 795.41162 | 633.5975 | ND |
| 85 | 98.81 | 0.56 | $C_{20}H_{39}O_7$ (3.152) | 391.2714 | 371.2172 | ND |
| 86 | 99.53 | 0.57 | $C_{39}H_{57}O_6$ (1.685) | 475.30817, 533.34947, 621.41711 | 179.11584, 451.48783, 577.68246, 603.59836 | ND |
| 87 | 100.29 | 1.85 | $C_{27}H_{41}O_4$ (1.717) | 429.30177, 475.30774 | 367.42174, 411.43779 | ND |
| 88 | 101.24 | 0.21 | $C_{30}H_{49}O_4$ (2.190) | 473.36460, 519.36979 | ND | ND |
| 89 | 102.05 | 1.32 | $C_{30}H_{47}O_4$ (2.306) | 471.34907, 517.35508, 943.70971 | 367.41415, 409.51672, 453.51813 | ND |
| 90 | 102.67 | 0.10 | $C_{39}H_{53}O_6$ (0.028) | 455.31789, 501.32245, 617.38478 | 497.49844, 573.61572 | ND |
| 91 | 103.00 | 0.17 | $C_{30}H_{47}O_5$ (0.394) | 487.34309, 533.34826, 975.69540 | 469.4995 | ND |
| 92 | 103.59 | 0.04 | $C_{29}H_{45}O_4$ (0.452) | 457.33254, 503.33759, 915.67143 | 395.50910, 439.45901 | ND |
| 93 | 103.90 | 0.20 | $C_{30}H_{47}O_4$ (1.075) | 471.34849, 517.35330, 943.70324 | 413.50334, 453.50566 | ND |

TABLE 4-continued

Mass spectrometry (m/z) analysis of 224C-F2. The corresponding chromatogram is reported in FIG. 9; putative structures in FIG. 10 and 11.

| Peak No. | Retention Time (min) | Relative Abundance | Formula ($\Delta$ ppm) | m/z* ([M − H]$^-$ in bold) | MS$^2$ | UV |
|---|---|---|---|---|---|---|
| 94 | 104.39 | 0.06 | $C_{30}H_{47}O_5$ (0.169) | 487.34298, 533.34853, 975.69146 | 455.4734 | 225, 290, 435 |

The greatest quorum quenching effects of 224C-F2 were observed in the retention time region of 21-49 min (FIG. 9), suggesting the presence of several distinct quorum quenching compounds (data not shown). Specifically, there are 22 compounds found in this region, 10 present at >1% relative abundance. These correspond to peak numbers, predicted formulas, and relative abundances of: 35 $C_{57}H_{24}O_2$ (2.67%), 36 $C_{27}H_{50}O_6$ (2.65%), 42 $C_{31}H_{50}O_6$ (1.43%), 43 $C_{30}H_{46}O_7$ (1.86%), 46 and 47 $C_{57}H_{23}O_2N_3$ (1.64% and 3.13%, respectively), 48 and 49 $C_{59}H_{25}O_3$ (1.45 and 1.07%, respectively), 50 $C_{41}H_{33}O_{16}$ (1.20%) and 51 $C_{30}H_{47}O_5$ (5.96%). Putative structures for 7 peaks were determined to be pentacyclic triterpenes (specifically, oleanene and ursene derivatives) based on accurate mass analysis, fragmentation patterns, and comparison with natural product databases (FIG. 10), and these collectively represent 16.37% in relative abundance. Of note, while present at relative abundance levels of <1% each, the putative structures of gallotannins (32, 33, 34) and ellagitannins (39) were also identified in the most active region of 224C-F2.

224C-F2 was also examined by HPLC-DAD and LC-FTMS for the presence of 5 compounds reported to be found in crude *C. sativa* leaf extracts, and it was determined that 224C-F2 does not contain chlorogenic acid, ellagic acid, hyperoside, isoquercitrin, or rutin.

TABLE 3

Inhibition of *S. aureus* quorum sensing by chestnut leaf extracts as detected by agr reporter strains.

| | | | Test Agent ($\mu$g mL$^{-1}$) | | |
|---|---|---|---|---|---|
| Strain ID | agr group | IC | 224 | 224C | 224C-F2 |
| AH1677 | I | IC$_{50}$ | 100 | 50 | 25 |
| | | IC$_{90}$ | ND | ND | 100 |
| AH430 | II | IC$_{50}$ | 25 | 50 | 12.5 |
| | | IC$_{90}$ | ND | ND | 100 |
| AH1747 | III | IC$_{50}$ | 25 | 12.5 | 1.56 |
| | | IC$_{90}$ | ND | 100 | 12.5 |
| AH1872 | IV | IC$_{50}$ | 100 | 100 | 25 |
| | | IC$_{90}$ | ND | ND | 100 |

A slightly higher level of growth inhibition was observed in the static MIC assays over that observed in the super-aerated reporter assay, but in all reporter strains, the MIC remained >100 $\mu$g mL$^{-1}$ for 224C-F2. No biofilm inhibitory or promoting activity of the extracts was noted.

Quorum quenching effects for 224C-F2 were observed at IC$_{50}$ values of 1.56-25 $\mu$g mL$^{-1}$, depending upon the strain tested (Table 3). The most potent quorum quenching activity was observed for agr III (IC$_{50}$ of 1.56 $\mu$g mL$^{-1}$), and the least for agr IV (IC$_{50}$ of 25 $\mu$g mL$^{-1}$). Significant inhibition of agr was observed for all agr alleles at sub-inhibitory concentrations for growth, indicating that the quorum-quenching activity is due to specific interference with agr, and not simply the result of a false positive due to growth inhibition.

Figure 4A:
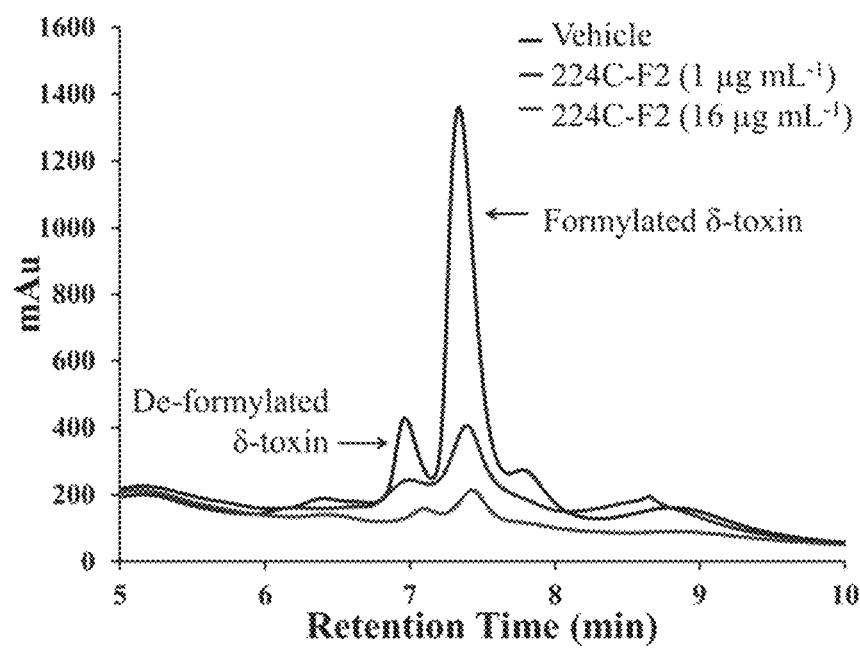
FIG. 4A shows data indicating 224C-F2 blocks MRSA exotoxin production. 224C-F2 demonstrates a dose-dependent effect in inhibition of de-formylated and formylated delta toxin, as illustrated in this HPLC chromatogram.
Figure 4B:
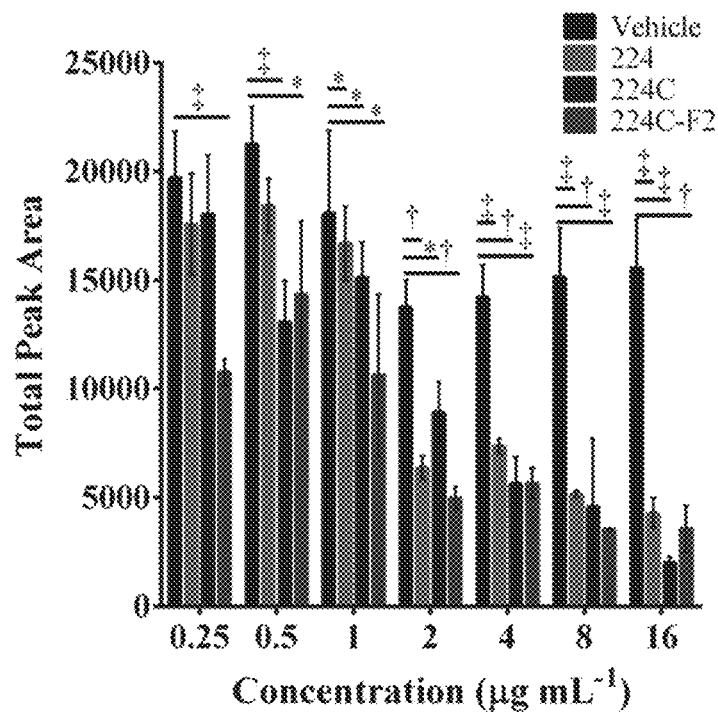
FIG. 4B show data on the quantification of delta-toxin confirmed the dose-dependent inhibitory activity of extracts, and the increased activity of the refined fraction 224C-F2 over 224 and 224C.

To verify the observed quorum quenching activity, downstream translational products of the quorum sensing system were assessed. HPLC quantification of $\delta$-toxin (FIG. 4A) from the supernatant of a heavy producer of exotoxins (NRS385, a USA 500, agr I, HA-MRSA isolate) revealed significant reduction (p<0.01) in production of $\delta$-toxin in 224C-F2 treated cultures at doses as low as 0.25 $\mu$g mL$^{-1}$ (FIG. 4B).

Figure 4C:
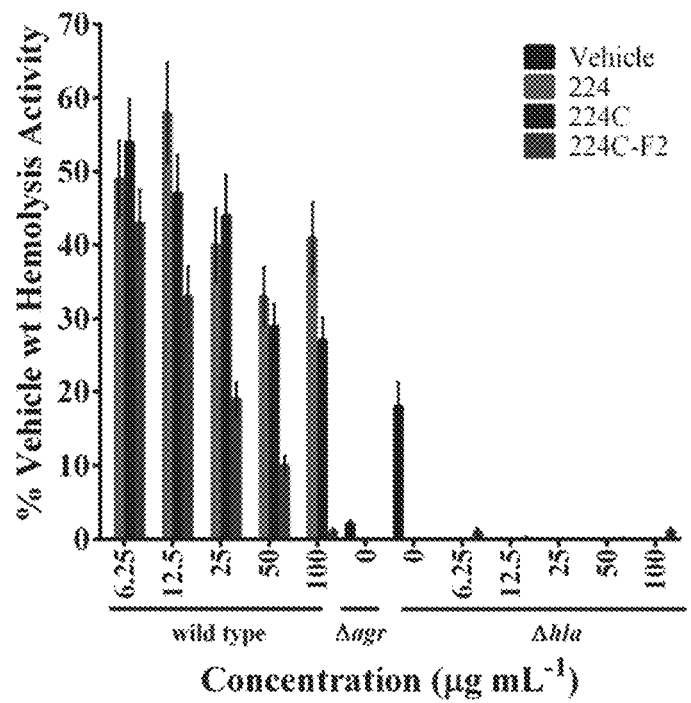
FIG. 4C shows data indicating extracts quench the hemolytic activity of both the *S. aureus* wild type and Δhla mutant, demonstrating that in addition to preventing production of α-hemolysin hemolysin (responsible for the major share of hemolytic activity), that extracts also inhibit PSM production, responsible for the observable hemolytic activity in hla mutant strains.
Figure 4D:
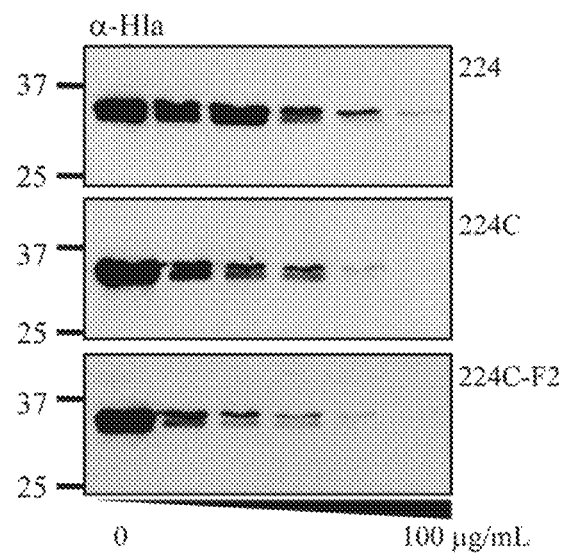
FIG. 4D shows data for USA300 (Δspa) was exposed to increasing doses of 224, 224C, 224C-F2, and vehicle control for 8 hrs. Western blot for α-hemolysin on supernatants demonstrated a dose-dependent decline in protein levels.

To verify the block in production of additional exotoxins, cultures of strain LAC (AH1263, a USA300, agr I, CA-MRSA isolate) and its isogenic agr (AH1292) and hla (AH1589) mutants were grown in the presence of the extracts and their supernatants were examined in a rabbit red blood cell lysis assay. In this assay, the majority of RBC lysis is attributed to the presence of $\alpha$-hemolysin in the culture supernatant. The presence of some lytic activity in the $\Delta$hla vehicle control suggests that some additional hemolytic activity (~18%) may be due to additional toxins in the supernatant, phenol soluble modulins (PSMs), in particular. Treatment of wild type with 224C-F2 resulted in significant (p<0.001) reduction in hemolytic activity in wild type strain at 6.25 $\mu$g mL$^{-1}$, and almost total loss of hemolytic activity at the concentration of 100 $\mu$g mL$^{-1}$. Treatment of the $\Delta$hla mutant demonstrated nearly total loss of hemolytic activity at 6.25 $\mu$g mL$^{-1}$ (FIG. 4C). Similar to the hemolysis assessment, when USA300 is exposed to increasing doses of all extracts (224, 224C, and 224C-F2), the level of $\alpha$-hemolysin protein production is markedly attenuated, with the most potent activity exhibited by 224C-F2 (FIG. 4D).

Sub Fraction Analysis

Figure 12:
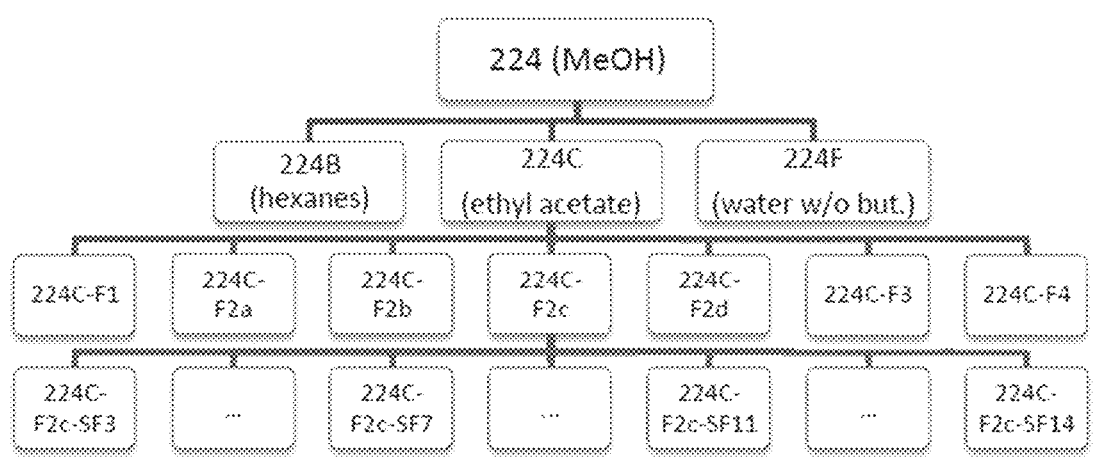
FIG. 12 shows scheme including sub fractions of 224C F2c semi-prep RP HPLC after flash chromatography.
Figure 13:
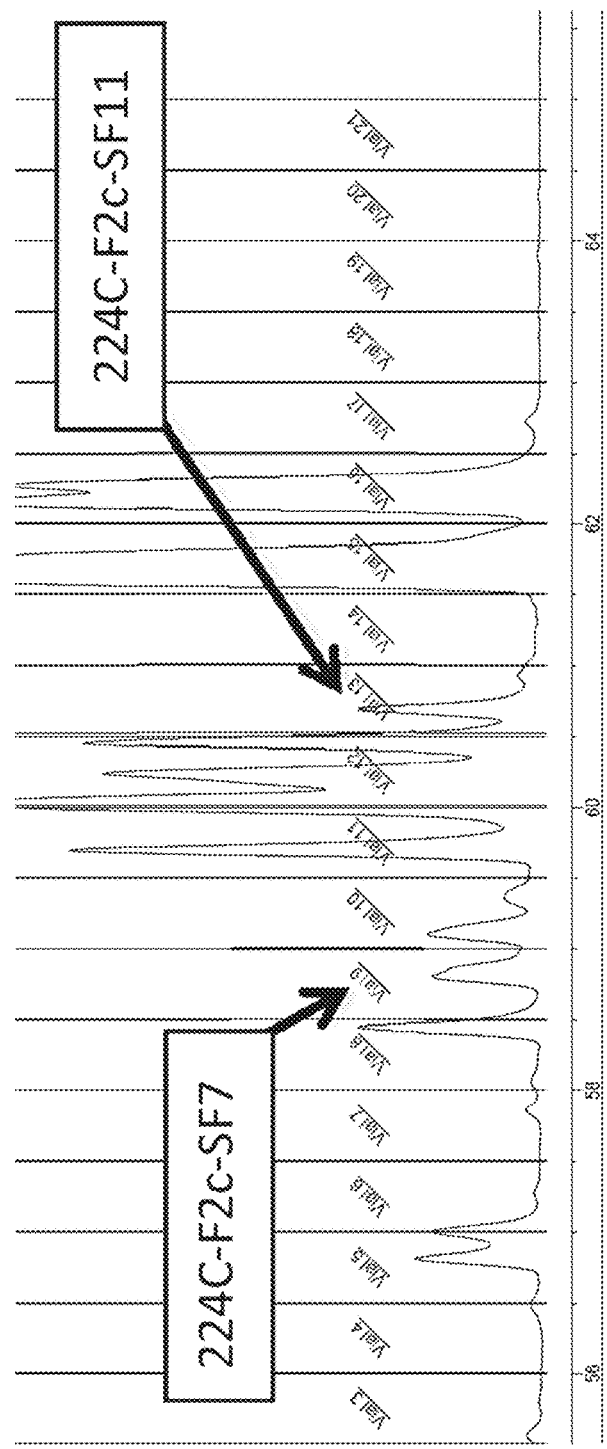
FIG. 13 shows RP HPLC and fractions.
Figure 14:
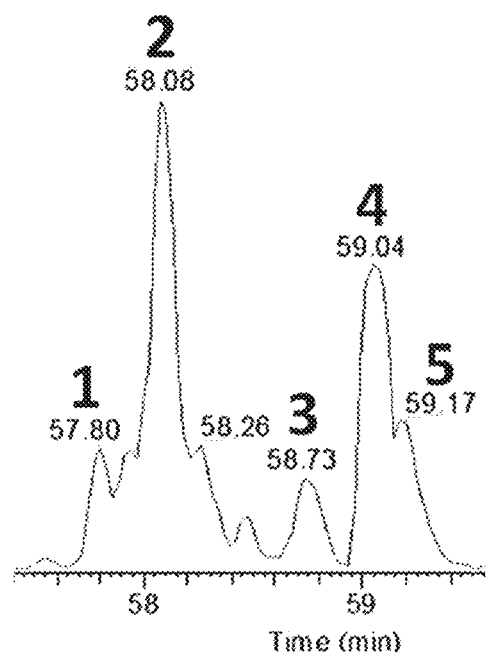
FIG. 14 shows LC-FTMS ESI negative of 224C F2c SF7.
Figure 15:
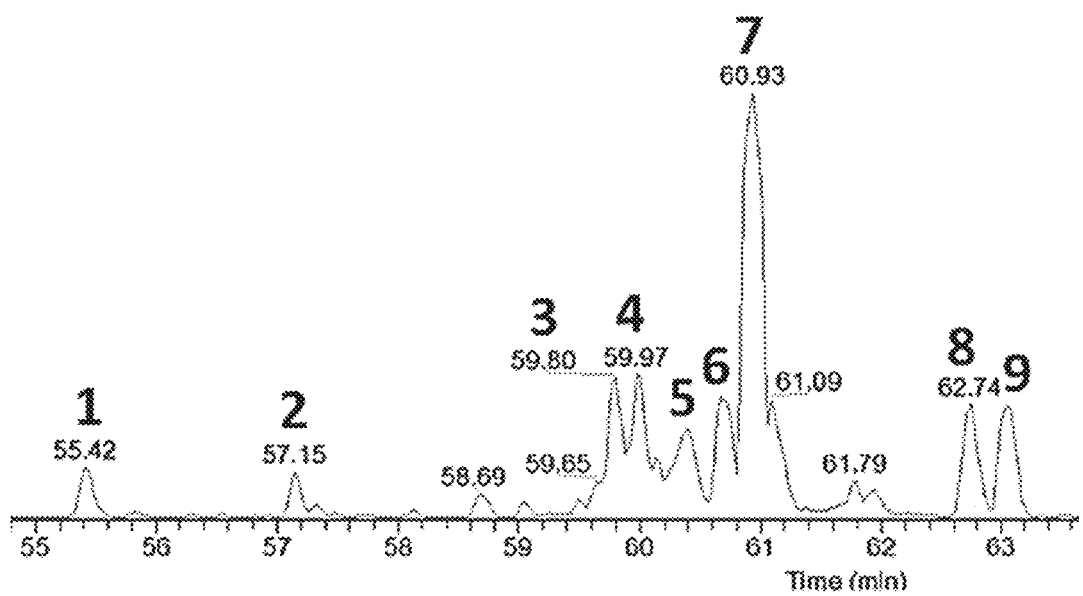
FIG. 15 shows LC-FTMS ESI negative of 224C F2c SF11.
Figure 16:
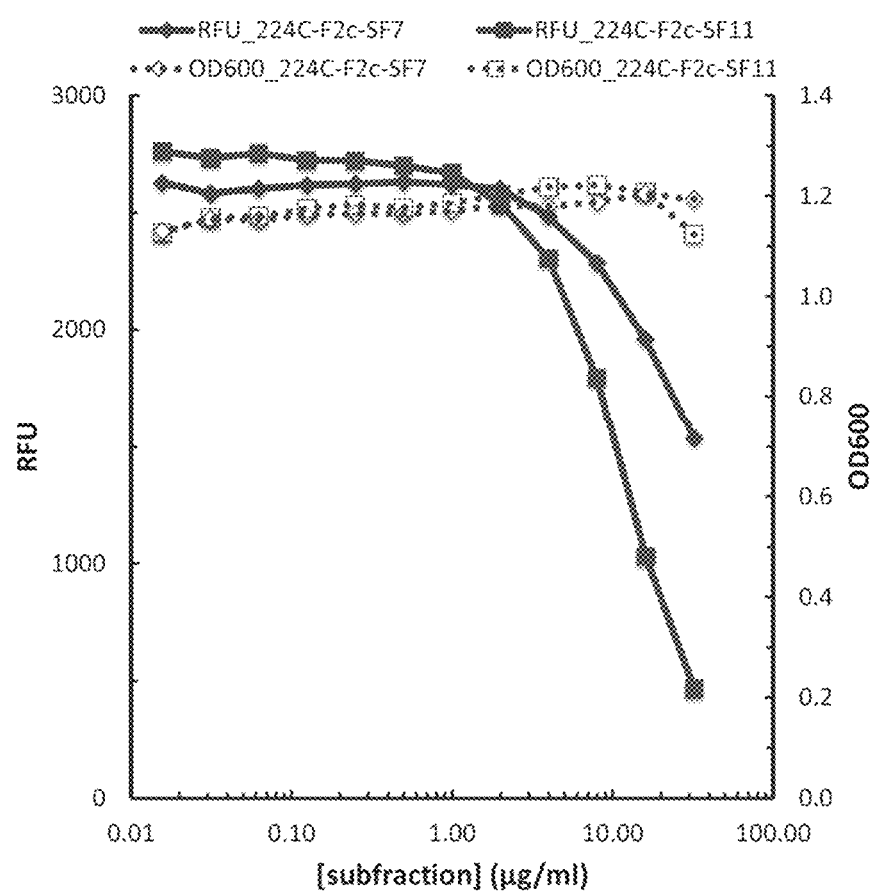
FIG. 16 shows Agr I activity and growth following treatment with subfractions 224C-F2c-SF7 and 224C-F2c-SF11 on *S. aureus* growth (measured in optical density, OD), accompanied by inhibition of agr I function (measured in fluorescent units, RFU) in a dose dependent fashion.

RP HPLC semi-prep chromatogram of 224C-F2c was performed at 314 nm (See FIG. 12). FIG. 13 shows Fractions 7 and 11 (note HPLC vial numbers do not correspond to the fraction numbers). FIGS. 14 and 15 show LC-FTMS ESI— for 224C-F2c-SF7 and SF11 respectively. FIG. 16 shows data indicating inhibition of agr without impacting growth. Table 4 Shows Data for 224C-F2c-SF7

| Peak | Retention Time (min) | Putative Formula ($\Delta$ ppm) | [M-H]$^-$ | MS-MS fragments |
|---|---|---|---|---|
| 1 | 57.8 | C39H61O7N (0.2) | 327.2185, 655.4447 | 593.5429, 611.5981, 637.6499 |
| 2 | 58.08 | C39H61O7N (0.2) | 327.2185, 575.4564, 615.4506, 655.4483 | 593.5785, 611.6195, 637.5610 |

-continued

| Peak | Retention Time (min) | Putative Formula (Δ ppm) | [M-H]$^-$ | MS-MS fragments |
|---|---|---|---|---|
| 3 | 58.73 | C39H31O15 (1.1) | 739.1666 | ND |
| 4 | 59.04 | C39H31O15 (1.7) | 739.167 | 285.1537, 453.2921, 575.3205, 593.3320 |
| 5 | 59.17 | C22H33O22N2 (0.1) | 677.152 | 285.1352, 531.2750, 617.2969 |

Table 5 Shows Data for 224C-F2c-SF11

| Peak | Retention Time (min) | Putative Formula (□ ppm) | [M-H]$^-$ | MS-MS fragments |
|---|---|---|---|---|
| 1 | 55.42 | C31H51O9 (−1.5) | 567.3530 | 535.5784 |
| 2 | 57.15 | C18H33O5 (−0.2) | 329.2333 | 211.2389, 229.2811, 311.3833 |
| 3 | 59.80 | C30H45O7 (1.5) | 517.3179 | 437.5225, 455.5107 |
| 4 | 59.97 | C30H45O7 (2.8) | 517.3179 | 437.4781, 455.5008 |
| 5 | 60.37 | C27H35ON4 (0.5) | 431.2813 | 369.4419, 413.4428 |
| 6 | 60.69 | C41H33O16 (−2.0) | 781.1759 | 285.1579, 495.3045, 635.3421 |
| 7 | 60.93 | C41H33O16 (−1.4) | 781.1762 | 285.1545, 495.2740, 635.3508 |
| 8 | 62.74 | C28H45O6 (2.2) | 477.3233, 523.3295, 955.6565 | 431.5300, 459.5256 |
| 9 | 63.04 | C24H35O5 (1.9) | 403.2798, 449.2562, 807.5076 | 357.4009, 385.4288 |

The invention claimed is:

1. A wound dressing or wound rinse comprising compounds in an extract, wherein the wound dress comprises an absorbent pad and optionally an adhesive, and wherein the extract comprises a leaf derived mixture of compounds from a *Castanea* plant wherein the extracting process comprises the steps of:
   mixing a leaf with methanol under conditions such that leaf compounds dissolves in the methanol and removing the methanol providing a methanol derived mixture of compounds,
   partitioning the methanol derived mixture of compounds in hexane and water providing a water derived mixture of compounds,
   partitioning the water derived mixture of compounds by mixing the water with ethyl acetate under conditions such that leaf compounds dissolve in the ethyl acetate and removing the ethyl acetate providing an ethyl acetate derived mixture of compounds; and
   purifying the ethyl acetate derived mixture of compounds by liquid chromatography through silica with a mobile phase comprising hexane and ethyl acetate;
   wherein the mobile phase comprises increasing amounts of ethyl acetate, and a mobile phase fraction is isolated comprising a leaf derived mixture of compounds which does not contain chlorogenic acid, ellagic acid, hyperoside, isoquercitrin or rutin.

2. The extract of claim 1, wherein the mixture of compounds comprises components having the following formulas and relative abundance,
   $C_{39}H_{59}O_8$ or $C_{38}H_{55}O_9$, or mixture, with a relative abundance of 0.1 to 0.9%;
   $C_{35}H_{59}O_6$ with a relative abundance of 0.1 to 0.9%;
   $C_{31}H_{49}O_6$ with a relative abundance of 1.0 to 2.0%;
   $C_{32}H_{51}O_7$ with a relative abundance of 0.1 to 0.9%;
   $C_{30}H_{48}O_5$ with a relative abundance of 3.0 to 5.0%;
   $C_{30}H_{48}O_6$ with a relative abundance of 6.0 to 8.0%; and
   $C_{30}H_{45}O_5$ with a relative abundance of 2.0 to 4.0%.

3. The extract of claim 2, further comprises additional components of different compounds having the following formula and relative abundance,
   $C_{35}H_{59}O_6$ with a relative abundance of 0.2 to 0.4;
   $C_{27}H_{23}O_{18}$ is with a relative abundance of 0.05 to 0.30;
   $C_{39}H_{31}O_{15}$ with a relative abundance of 0.50 to 0.80;
   $C_{17}H_{11}O_8$ or $C_{20}H_{11}O_4N_2$, or mixture, with a relative abundance of 0.5 to 1.0; and
   $C_{34}H_{29}O_{15}$ with a relative abundance of 0.2 to 0.4%.

* * * * *